United States Patent
Lund et al.

(10) Patent No.: US 9,968,428 B2
(45) Date of Patent: May 15, 2018

(54) SURGICAL TOOLS, SYSTEMS, AND RELATED IMPLANTS AND METHODS

(75) Inventors: Jonathan J. Lund, Minneapolis, MN (US); Anthony J. Ferrazzo, New Prague, MN (US); Kory P. Hamel, Bloomington, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 392 days.

(21) Appl. No.: 13/990,017

(22) PCT Filed: Dec. 16, 2011

(86) PCT No.: PCT/US2011/065480
§ 371 (c)(1),
(2), (4) Date: May 28, 2013

(87) PCT Pub. No.: WO2012/083159
PCT Pub. Date: Jun. 21, 2012

(65) Prior Publication Data
US 2013/0253260 A1    Sep. 26, 2013

Related U.S. Application Data

(60) Provisional application No. 61/423,810, filed on Dec. 16, 2010.

(51) Int. Cl.
*A61F 2/04* (2013.01)
*A61F 2/00* (2006.01)
(Continued)

(52) U.S. Cl.
CPC ........ *A61F 2/0045* (2013.01); *A61B 17/0401* (2013.01); *A61B 17/06109* (2013.01);
(Continued)

(58) Field of Classification Search
CPC ......... A61B 2017/00805; A61F 2/0004; A61F 2/0022; A61F 2002/0072
See application file for complete search history.

(56) References Cited

U.S. PATENT DOCUMENTS

| 5,112,344 A | 5/1992 | Petros |
| 5,611,515 A | 3/1997 | Benderev et al. |

(Continued)

FOREIGN PATENT DOCUMENTS

| WO | 98/35616 A1 | 8/1998 |
| WO | 0239890 A2 | 5/2002 |

(Continued)

OTHER PUBLICATIONS

First Examination Report for Australian Application No. 2016202128, dated Mar. 24, 2017, 4 pages.
(Continued)

*Primary Examiner* — Thaddeus Cox
(74) *Attorney, Agent, or Firm* — Brake Hughes Bellermann LLP

(57) ABSTRACT

Described are implants and tools for use in treating pelvic conditions such as incontinence, including urinary incontinence in a male or female, for example an incontinence sling and delivery system that can include a sling implant and delivery tool system, wherein the implant can include a mesh sling and one or more anchors provided at or extending from a portion of the sling to facilitate tissue fixation; the delivery tool system can include at least a tunneler having a lumen, and an insertion tool; and wherein useful methods can involve inserting the tunneler through an incision and into a pelvic region of a patient, connecting the insertion tool to the sling, and inserting the sling into the tunneler to place the sling to provide tissue support.

21 Claims, 21 Drawing Sheets

(51) Int. Cl.
*A61B 17/04* (2006.01)
*A61B 17/06* (2006.01)
*A61B 17/34* (2006.01)
A61B 17/02 (2006.01)
A61B 17/00 (2006.01)
A61B 17/32 (2006.01)

(52) U.S. Cl.
CPC ...... *A61B 17/3468* (2013.01); *A61B 17/0218* (2013.01); *A61B 2017/00805* (2013.01); *A61B 2017/042* (2013.01); *A61B 2017/0409* (2013.01); *A61B 2017/0427* (2013.01); *A61B 2017/320056* (2013.01)

(56) References Cited

U.S. PATENT DOCUMENTS

| | | | |
|---|---|---|---|
| 5,842,478 | A | 12/1998 | Benderev et al. |
| 5,860,425 | A | 1/1999 | Benderev et al. |
| 5,899,909 | A | 5/1999 | Claren et al. |
| 6,039,686 | A | 3/2000 | Kovac |
| 6,042,534 | A | 3/2000 | Gellman et al. |
| 6,110,101 | A | 8/2000 | Tihon et al. |
| 6,478,727 | B2 | 11/2002 | Scetbon |
| 6,638,211 | B2 | 10/2003 | Suslian et al. |
| 7,070,556 | B2 | 7/2006 | Anderson et al. |
| 7,686,760 | B2 | 3/2010 | Anderson et al. |
| 2002/0055748 | A1* | 5/2002 | Gellman et al. ............... 606/139 |
| 2003/0069595 | A1 | 5/2003 | Phung et al. |
| 2004/0087970 | A1* | 5/2004 | Chu ................ A61B 17/00234 606/119 |
| 2005/0245787 | A1 | 11/2005 | Cox et al. |
| 2005/0250977 | A1 | 11/2005 | Montpetit et al. |
| 2006/0025783 | A1 | 2/2006 | Smith et al. |
| 2006/0089633 | A1 | 4/2006 | Bleich et al. |
| 2006/0122457 | A1 | 6/2006 | Kovac et al. |
| 2006/0168761 | A1 | 8/2006 | Christensen et al. |
| 2006/0195007 | A1 | 8/2006 | Anderson et al. |
| 2006/0195010 | A1 | 8/2006 | Arnal et al. |
| 2006/0195011 | A1 | 8/2006 | Arnal et al. |
| 2006/0217589 | A1* | 9/2006 | Wan et al. ...................... 600/29 |
| 2006/0235262 | A1 | 10/2006 | Arnal et al. |
| 2006/0260618 | A1 | 11/2006 | Hodroff et al. |
| 2006/0287571 | A1 | 12/2006 | Gozzi et al. |
| 2007/0038017 | A1* | 2/2007 | Chu ................... A61B 17/0482 600/37 |
| 2007/0112361 | A1* | 5/2007 | Schonholz ....... A61B 17/0234 606/151 |
| 2009/0192347 | A1* | 7/2009 | Davila ............ A61B 17/06109 600/37 |
| 2010/0256442 | A1* | 10/2010 | Ogdahl et al. .................. 600/30 |
| 2011/0034759 | A1 | 2/2011 | Ogdahl et al. |
| 2011/0034942 | A1* | 2/2011 | Levin et al. .................. 606/151 |

FOREIGN PATENT DOCUMENTS

| | | | |
|---|---|---|---|
| WO | 02069781 | A2 | 9/2002 |
| WO | 02/078548 | A1 | 10/2002 |
| WO | 2006028828 | A2 | 3/2006 |
| WO | 2007/016083 | A1 | 2/2007 |
| WO | 2007014120 | A2 | 2/2007 |
| WO | 2007016083 | A1 | 2/2007 |
| WO | 2007/097994 | A2 | 8/2007 |
| WO | 2007126632 | A2 | 11/2007 |
| WO | WO 2007126632 | A2 * | 11/2007 ....... A61B 17/06109 |
| WO | 2007149348 | A2 | 12/2007 |
| WO | 2008013867 | A1 | 1/2008 |
| WO | 2011106419 | A1 | 9/2011 |

OTHER PUBLICATIONS

Office Action for Canadian Application No. 2,818,945, dated Oct. 27, 2017, 5 pages.

International Preliminary Report on Patentability for International Application No. PCT/US2011/065480, dated Jun. 18, 2013, 7 pages.

International Search Report for International Application No. PCT/US2011/065480, dated Apr. 9, 2012, 2 pages.

* cited by examiner

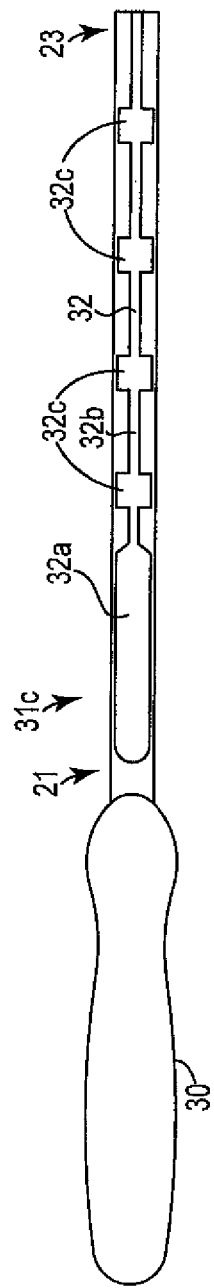
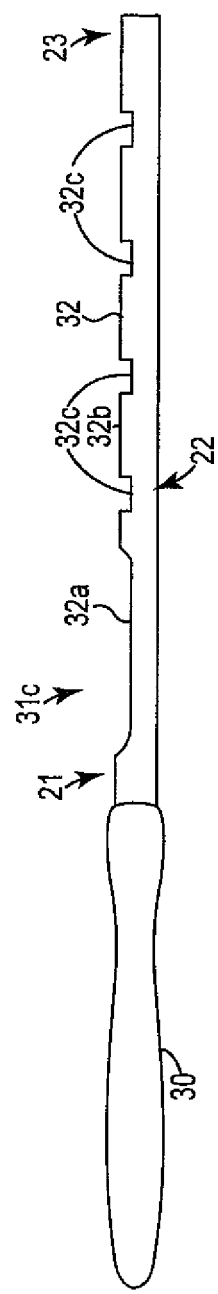
Fig. 4E
Fig. 4F

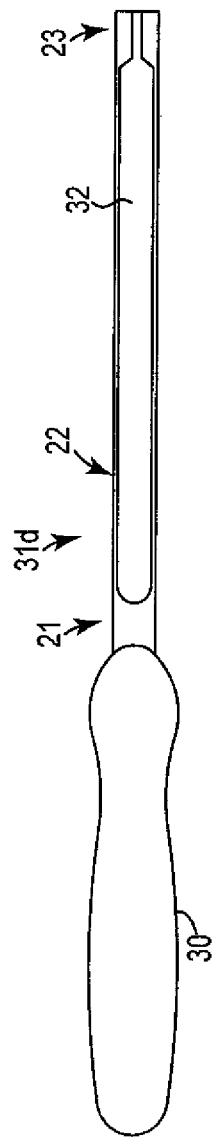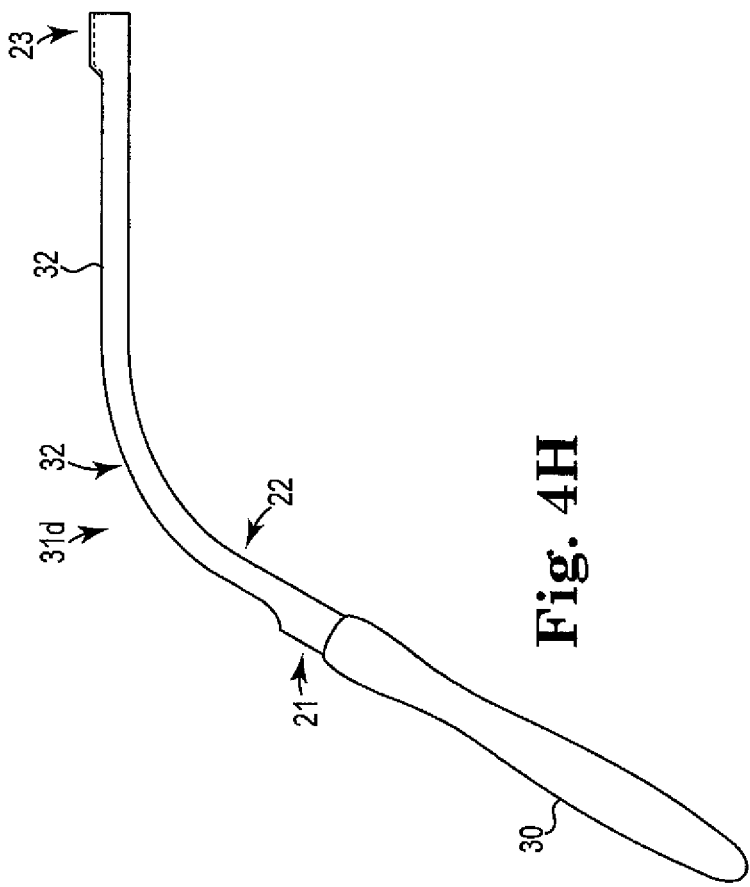
Fig. 4G
Fig. 4H

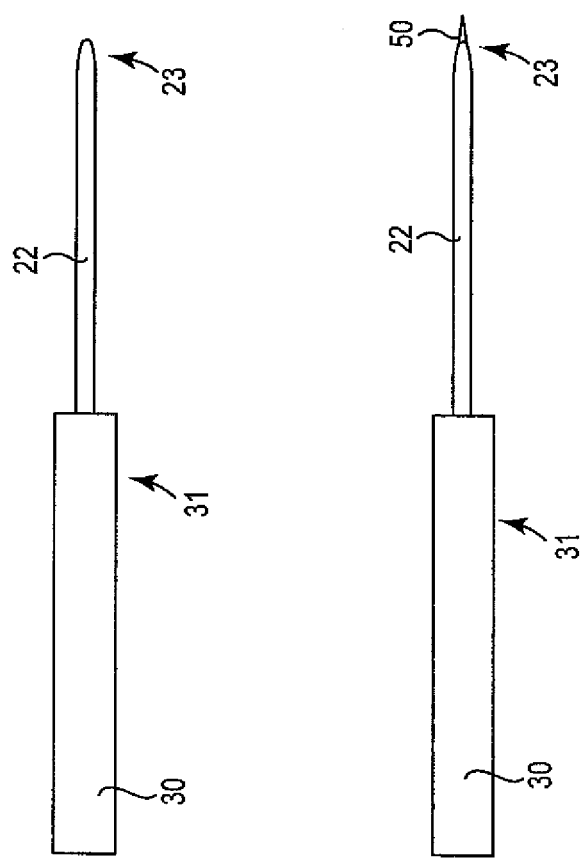

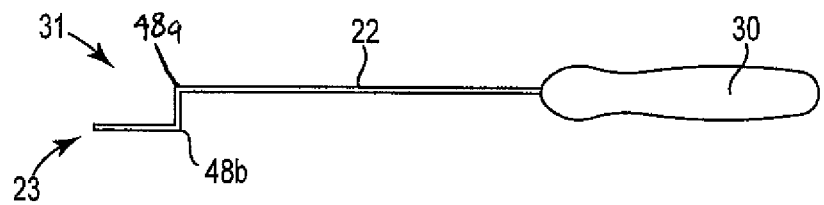
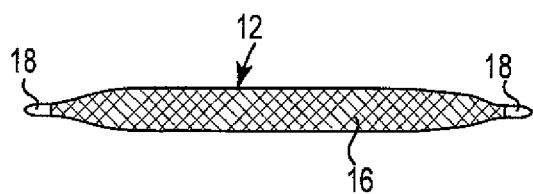
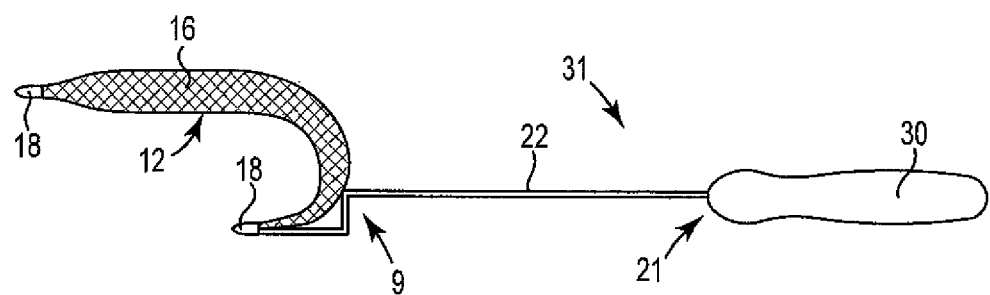
Fig. 15

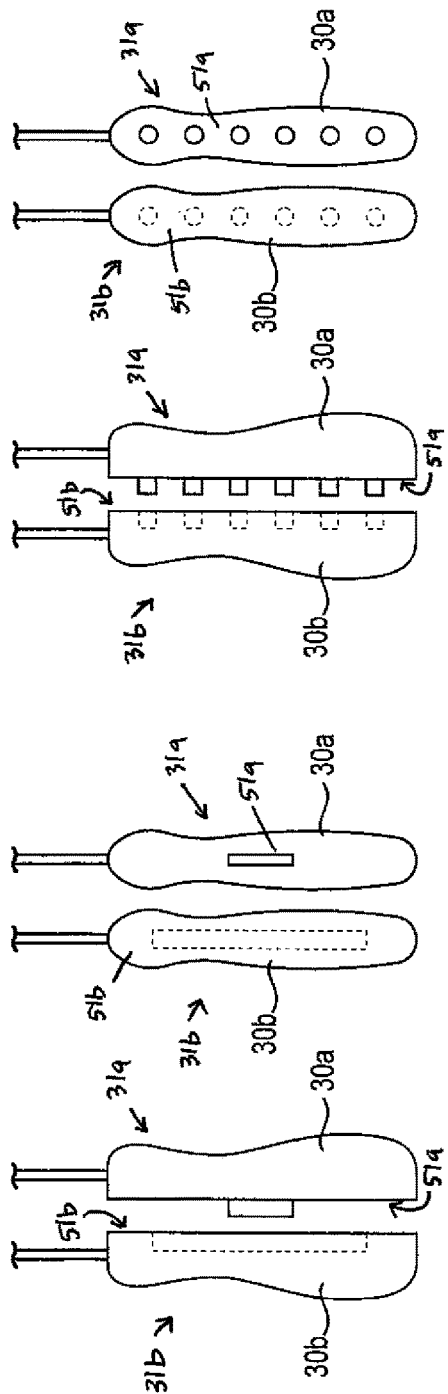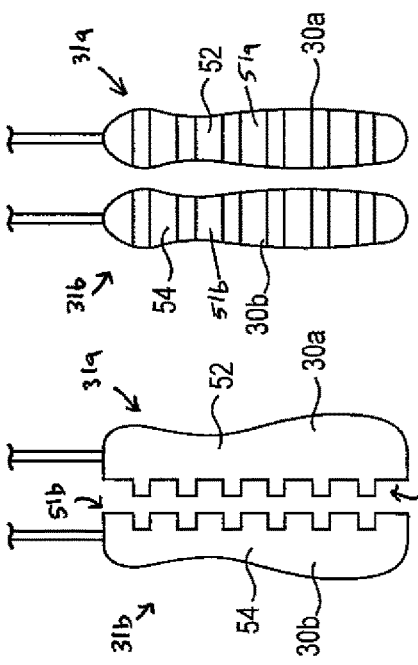

SURGICAL TOOLS, SYSTEMS, AND RELATED IMPLANTS AND METHODS

PRIORITY CLAIM

This application claims the benefit from International No. PCT/US2011/065480, which was granted an International filing date of Dec. 16, 2011, which in turn claims priority to U.S. Provisional Application Ser. no. 61/423,810, filed Dec. 16, 2010, and entitled "INCONTINENCE SLING AND DELIVERY SYSTEM AND METHOD," which applications are incorporated herein by reference in their entireties.

FIELD OF THE INVENTION

The following description relates generally to surgical tools, systems of tools, and related methods, including those that involve placing an implant using a multi-tool delivery system, for treating a pelvic condition such as incontinence, prolapse, or the like.

BACKGROUND

Pelvic conditions such as urinary incontinence, fecal incontinence, and prolapse are a significant health concern worldwide. Men, women, and children of all ages can suffer from urinary incontinence or involuntary loss of urinary control. The lives of those who suffer urinary incontinence are perpetually interrupted by thoughts of ensuring ready access to a restroom. Everyday activities such as attending a theater or sporting event can become unpleasant. Sufferers often begin to avoid social situations in an effort to reduce the stress associated with their condition.

A variety of treatment options are currently available, but improvements are continually desired. Some current treatments include external devices, behavioral therapy (such as biofeedback, electrical stimulation, or Kegel exercises), prosthetic devices, and surgery. Depending on the age, medical condition, and personal preference of a patient, surgical procedures can be used to completely restore continence.

In the urology field, needles, suture passers and ligature carriers are used in a variety of procedures, many of which are designed to treat incontinence. A pubomedial sling procedure involves placement of a surgical implant in the form of a urethral sling to stabilize or support the bladder neck or urethra, to treat incontinence. Descriptions of various sling procedures are included at U.S. Pat. Nos. 5,112,344; 5,611,515; 5,842,478; 5,860,425; 5,899,909; 6,039,686; 6,042,534; 6,110,101; 6,478,727; 6,638,211; U.S. Publication Nos. 2010/0256442 and 2011/0034759; PCT Publication Nos. WO 02/39890; WO 2011/106419 and WO 02/069781.

Some pubomedial sling procedures extend a sling from the rectus fascia in the abdominal region to a position below the urethra and back again to the rectus fascia. Other procedures, used in particular to treat male stress urinary incontinence (SUI), can include introducing and deploying a mesh sling implant via multiple incisions. Namely, a first medial (e.g., perineal) incision can be made to expose the bulb of the urethra, which provides the first sling fixation point. Following that incision, two smaller incisions can be made in the creases where the patient's thighs join the pelvis to allow introducer needles to pass through the skin into the perineal incision. The sling can then be connected to the needles and pulled into position, with the ends of the sling drawn outside of the body to allow for tensioning before being trimmed at skin level.

While many of the above-identified methods and systems currently provide efficacious options for treating pelvic conditions including but not limited to prolapse and urinary incontinence in male and female patients, improved methods, devices, tools, and systems are continuously pursued.

SUMMARY OF THE INVENTION

The invention relates generally to tools, implants, and systems that involve an implant and a multi-tool delivery system, and related methods. The implant can be for treating a pelvic condition in a male or female patient, and can include a support portion, multiple extension portions, and an anchor to secure the implant to supportive tissue. Certain embodiments of implants for treating urinary incontinence or vaginal prolapse can include a tissue support portion for placement below a urethra or bladder, and two opposing extension portions that can be placed at tissue paths extending from a location to support the urethra or bladder, to opposing (a left and a right) obturator foramen. A tissue path may extend toward and end at pelvic fascia without reaching or passing into or through the obturator foramen. Alternately, a tissue path may extend to the obturator foramen. In still other embodiments the tissue path may extend through an obturator foramen. The methods can involve two opposing tissue paths, as described, one on each of a left and a right side of the patient. The implant can include or consist of a single integral strip (e.g., mesh strip) or two or three pieces that can be assembled to produce an implant that includes a support portion and two extension portions.

A multi-tool delivery system can include multiple tools selected from a tunneler tool (e.g., a stylet), an insertion tool, and an optional core tool.

The tunneler tool can extend from a proximal end external to a patient, to a distal end internal to the patient and adjacent supportive tissue. The tunneler tool can include a shaft that contains a passage lumen (e.g., an open inner channel) and that is adapted for insertion into the pelvic region of the patient through an incision in the patient that may be a vaginal incision or another medial (perineal) or otherwise external incision. The tunneler tool can be inserted into the incision and create a tissue path by pushing the distal end of the tunneler tool through tissue, toward the supportive tissue. To avoid excessive trauma, the distal end of the tunneler tool, which includes a distal end opening, can be filled or plugged during insertion of the tunneler tool to produce the tissue path. The distal end opening can be plugged by a distal end of a separate tool, such as a distal end of a core tool, or a distal end of an insertion tool. Alternately, an anchor of the implant can be used to plug the distal end opening, whereby the anchor is engaged at a distal end of the insertion tool, and the assembly of the insertion tool and the engaged anchor is inserted within the tunneler tool to place the anchor within the distal end opening.

Once the tunneler tool is passed through tissue to create a tissue path between an incision and a region of supportive tissue, the core tool, insertion tool, or insertion tool-and-anchor assembly used to plug the distal end opening of the tunneler tool, can be removed, leaving full access along the length of the open internal channel of the tunneler tools to the region of supportive tissue. The insertion tool can the be connected to a portion of the sling implant, e.g., the sling anchor or self-fixating tip, and the distal end of the insertion tool, engaged with the anchor, can be inserted into the open internal channel to place the implant or its respective anchor at or near the supportive tissue. The tunneler tool can be removed before or after final placemen of the anchor within supportive tissue.

A tunneler tool can completely enclose the open inner channel, or can include an exterior channel or slot (i.e., longitudinal opening) extending along a length of the tunneler tool, such as along a length of the distal end of the tunneler tool shaft. In embodiments of tunneler tools that include a longitudinal channel or s slot, a portion of the implant (e.g., a mesh portion) can be adapted to ride or travel on the outside of the tunneler tool, while the insertion tool shaft (or at least a distal portion of the insertion tool shaft), and an anchor of the sling implant, ride or travel within the inner open channel. In other embodiments, the insertion tool shaft, implant (in its entirety), and anchor, can all travel within the open internal channel of the tunneler tool during placemen of the implant.

Once desired deployment position and tension for the implant are achieved, the insertion tool is generally held in place while the tunneler tool is withdrawn, thereby exposing the sling anchor. The anchor can then be fixated to desired target tissue, or later anchored upon similarly positioning an opposing anchor of the sling implant at an opposite side of the patient.

Certain described embodiments allow physicians to adjust tension within an implant, prior to anchoring the implant to target tissue (supportive tissue) at opposing sides of the patient. A single incision (e.g., perineal in males, vaginal in females) can be used to facilitate an open and easily visualized surgical field. Further, needle (insertion tool shaft) placement and maneuvering are simplified relative to other known surgical systems and procedures, by allowing the physician to focus on first establishing a correct needle path (one on each side of the patient), before separately addressing placement and anchoring of the mesh. Conventional methods require the physician to focus on establishing the path and placement of the mesh at the same time, which can introduce unsafe and imprecise procedural complexities.

Advantageously, embodiments of a tools, systems, and methods as described allow a step of forming a tissue path using a tunneler tool, to be a separate step relative to a step of placing an end of an implant at supportive tissue. In specific, after formation of a tissue path using a tunneler tool, an insertion tool can position an end of an implant at a location near supportive tissue. The tunneler tool can be separated from the insertion tool and withdrawn from the tissue path and the patient, and freed from the implant at the distal end of the insertion tool. According to certain preferred embodiments, the insertion tool can be used to place the distal end of the implant (e.g., a self-fixating tip) at supportive tissue, after the tunneler tool has been used to create the tissue path and subsequently removed from the tissue path and the patient.

In one aspect, the invention relates to a delivery tool system that includes: a tunneler tool comprising a tunneler shaft comprising a proximal end, a distal end, and an internal channel; a longitudinal opening along a length between the proximal end and the distal end; and a distal end opening in communication with the internal channel and in communication with the longitudinal opening. The system also includes an insertion tool comprising a proximal end, a distal end, and an elongate shaft between the proximal end and the distal end. At least the distal end of the insertion tool can be located within the internal channel of the tunneler tool.

In another aspect the invention relates to a delivery tool system. The delivery tool system includes a first tunneler tool and a second tunneler tool, each including: a tunneler shaft comprising a proximal end, a distal end, and an internal channel; a longitudinal opening along a length between the proximal end and the distal end; and a distal end opening in communication with the internal channel and in communication with the longitudinal opening. The system also includes a first and a second insertion tool, each comprising a proximal end, a distal end, and an elongate shaft between the proximal end and the distal end. At least the distal end of the each insertion tool can be located within the internal channel of a tunneler tool.

In another aspect the invention relates to delivery tool system. The system includes a tunneler tool that includes: a tunneler shaft having a proximal end, a distal end, and an internal channel; a longitudinal opening along a length between the proximal end and the distal end; and a distal end opening in communication with the internal channel and in communication with the longitudinal opening. The system also includes an insertion tool having a proximal end, a distal end, and an elongate shaft between the proximal end and the distal end. The insertion tool can be located within the internal channel of the tunneler tool. The system includes a plug for the distal end opening. The system includes an implant having a support portion, two extension portions, and an anchor at an end of each extension portion. At least one anchor is adapted to engage a distal end of at least one of the two insertion tools.

In another aspect, the invention relates to a method of treating a pelvic condition in a patient. The method includes: providing a tunneler tool, an insertion tool, and an implant; creating an incision in the patient; using the tunneler tool to form a tissue path between the incision and a region of supportive tissue; engaging an end of the implant at a distal end of the insertion tool; with the tunneler tool in the tissue path, advancing the end of the implant through an internal channel of the tunneler tool from a proximal end of the tunneler tool to a distal end of the tunneler tool at the region of supportive tissue; removing the tunneler tool from the tissue path; and before or after removing the tunneler tool, using the insertion tool to place the distal end of the implant in the supportive tissue.

In another aspect, the invention relates to method of assembling a system. The method includes: providing a tunneler tool having a proximal end, a distal end, an internal channel, and a longitudinal opening; providing an insertion tool having a proximal end, a distal end, and a shaft; providing an implant having a tissue support portion, a first extension portion, and a first anchor at an end of the first extension portion; engaging the distal end of the insertion tool with the anchor; advancing the anchor through the internal channel of the tunneler tool; and separating the tunneler tool from the shaft of the insertion tool by passing the shaft through the longitudinal opening of the tunneler tool.

BRIEF DESCRIPTION OF THE DRAWINGS

FIG. 6F illustrates an embodiment of an insertion tool as described.

FIG. 15 shows an example of an insertion tool and implant combination as described.

FIGS. 18A, 18B, 18C, 18D, 18E, and 18F, all side views, illustrate insertion tools as described.

Figure 1A:
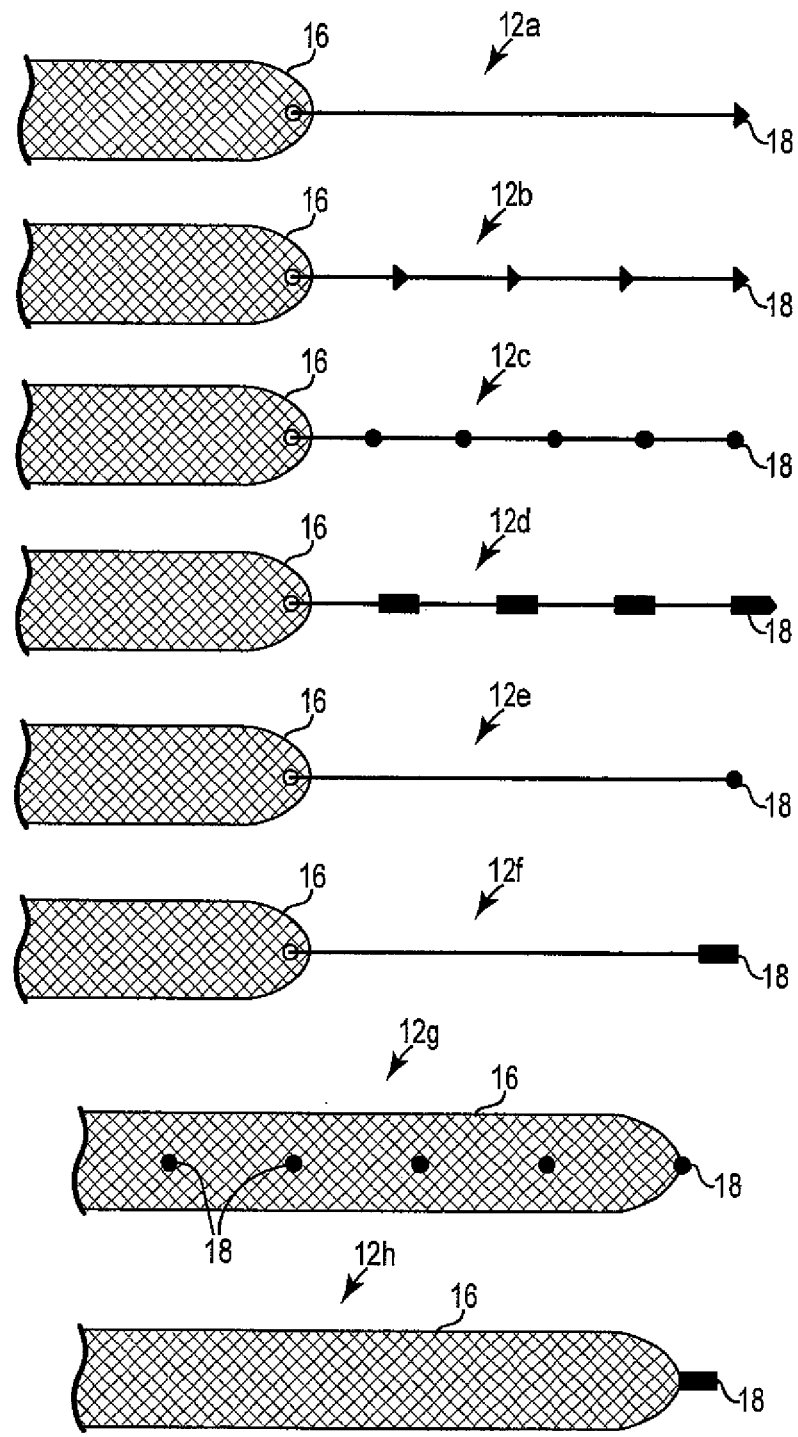
FIGS. 1A and 1B illustrate examples of implants as described.

All figures are not to scale.

DETAILED DESCRIPTION

Described are surgical instruments, assemblies, systems, and implantable articles for treating disorders such as urinary incontinence (e.g., stress urinary incontinence (SUI)) and other pelvic conditions. In various embodiments, the described instruments, assemblies, systems, etc., can be specifically directed to uses in treating urinary incontinence in men. However, these and other embodiments of described instruments, assemblies, systems, etc., will also be useful to treat urinary incontinence, fecal incontinence, prolapse, and other pelvic conditions in a female anatomy as well (e.g., via a vaginal incision). Exemplary devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies and the like.

Various tools, device structures, components, methods and techniques described and depicted in U.S. Pat. Nos. 7,686,760, 7,070,556 are envisioned for use, in whole or in part, with the present invention. As such, the entire disclosures of the above-referenced patents are incorporated herein by reference in their entirety. See also, e.g., U.S. Publication Nos. 2010/0256442 and 2011/0034759, and PCT Publication No. WO 2011/106419.

Certain embodiments involve surgical instruments, assemblies, combinations (e.g., of implants and tools), and implantable articles for treating pelvic floor disorders such as prolapse (e.g., vaginal prolapse), incontinence (urinary and fecal incontinence), conditions of the pelvic floor such as the perineal body, conditions of levator muscle (such as a component of levator muscle), conditions of the levator hiatus, and combinations of two or more of these. According to various embodiments, a surgical implant can be used to treat a pelvic condition, wherein the method includes placing an implant in a manner to support tissue of the pelvic region in a male or female. Methods involve the use of an implant and one or more tools of a multi-component assembly, the implant including at least one self-fixating tip that becomes implanted into supportive tissue of the pelvic region.

An implant can include a tissue support portion (or "support portion") that can be used to support pelvic tissue such as the bladder or urethra (which includes any location of the bladder, urethra, bladder neck, mid-urethra, or proximal end of the urethra), vaginal tissue, tissue of the perineum, coccygeus, levator ani, levator hiatus, rectum, etc., as discussed herein. During use, the tissue support portion can be placed in contact with tissue to be supported, or adjacent tissue, and optionally attached or secured to that tissue by use of one or more of a suture, biological adhesive, mechanical attachment, or another mode of attachment.

An implant can additionally include one or more extension portion (otherwise known as "end" portions or "arms") attached to the tissue support portion. Examples of pelvic implants are described in the following exemplary documents: U.S. Pat. No. 7,070,556; United States patent publication numbers 2005/0245787; 2006/0195011; 200610195010; 2006/0235262; 2006/0287571; 2006/0195007; 2006/0260618; 2006/0122457; 2005/0250977; and International patent application number PCT/US20061028828, having an International Filing Date of Jul. 25, 2006; International patent application number PCT/US2007/016760, having an International Filing Date of Jul. 25, 2007; International patent application number PCT/US2007/014120, having an International Filing Date of Jun. 15, 2007; and International patent publication WO 2007/097994, the entireties of each of these disclosures being incorporated herein by reference. Extension portions are elongate pieces of material that extend from the tissue support portion and either are or can be connected to the tissue support portion, and are useful to attach to an anatomical feature of the pelvic region (e.g., using a self-fixating tip) to thereby provide support for the tissue support portion and the supported tissue. One or multiple (e.g., one, two, or four) extension portions can extend from the tissue support portion as elongate "ends," "arms," or "extensions," useful to attach to tissue in the pelvic region.

An implant may include portions or sections that are synthetic or of biological material (e.g., porcine, cadaveric, etc.). Extension portions may be, e.g., a synthetic mesh such as a polypropylene mesh. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, Monarc®, Advance®, and Miniarc® for treating urinary incontinence.

An example of a particular type of pelvic implant is the type that includes supportive portions including or consisting of a central support portion and either two, four, or six elongate extension portions extending from the central support portion. An implant that has exactly two extension portions can be of the type useful for treating, e.g., urinary incontinence, anterior vaginal prolapse, or posterior vaginal prolapse. An implant having four or six extension portions can be useful for treating combinations of these conditions. The term "supportive portions" refers to extension portions and tissue support portions and does not include optional or appurtenant features of an implant or implant system such as a sheath, self-fixating tip or other type of connector for attaching the implant to an insertion tool, guide, etc.

Examples of implants for treating urinary incontinence, e.g., urethral slings, can include a central support portion (e.g. "support portion" or "tissue support portion") and only two extension portions, and may take the form of an integral mesh strip. An exemplary urethral sling can be an integral mesh strip with supportive portions consisting of or consisting essentially of a central support portion and two extension portions. Examples of urethral slings for treating male urinary incontinence can have a widened central support portion, as discussed, for example, in Assignee's copending United States patent publication numbers 2006/0287571 and 2006/0235262. Other exemplary urethral sling implants are described in Assignee's U.S. Pat. No. 7,070,556; United States publication numbers 2006/0195010, 2006/0195007, 2010/0256442 and 2011/0034759; and International application numbers WO 2007/097994, WO 2007/014120 and WO 2011/106419; among others.

Examples of implants for treating vaginal prolapse can comprise a central support portion and from two to four to six extension portions, and may take the form of an integral piece .of mesh or multiple pieces of mesh or mesh and biologic material, attached in a modular fashion. See, e.g., Assignee's copending United States patent publication numbers 2006/0260618; 2005/0245787; 2006/0122457; 2005/0250977; and International patent application number PCT/2006/028828; among others.

Examples of implants for treating conditions of the pelvic floor, such as to support tissue of the perineal body, to treat levator avulsion, to treat levator ballooning, to support or repair levator ani muscle, to tighten or reduce the size of levator hiatus, to treat vaginal prolapse, or to treat fecal incontinence, may take the form of an integral piece of mesh or multiple pieces of mesh or mesh and biologic material, attached in a modular fashion. See, e.g., International patent application number PCT/US2007/016760, filed Jul. 25, 2007, by Kimberly Anderson, entitled SURGICAL ARTICLES AND METHODS FOR TREATING PELVIC CONDITIONS.

In use, an implant can be placed to support tissue of a pelvic region by placing the tissue support portion in a position to support that tissue, and by placing each extension portion or an end of each extension portion at supportive tissue, in a manner to secure the extension portion (such as a self-fixating tip) to the supportive tissue, also in the pelvic region. In exemplary uses, each extension portion can extend from the location of attachment with the tissue support portion, through pelvic tissue, and optionally be attached to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. Alternate supportive tissues, for use in supporting an implant for treating a different condition, e.g., prolapse, may include a ligament (sacrospinous ligament), tendon, or muscle in the pelvic region such as an arcus tendineus, sacrospinous ligament, or levator muscle. Dimensions, shapes, and overall designs of implants and tools (tunneler tool, insertion tool, and core tool) as described herein can be designed to allow access to such supportive tissue and placement of an implant to that supportive tissue, through a single incision in a patient such as a single medial or vaginal incision.

Dimensions of an implant can be as desired and useful for any particular installation procedure, treatment, patient anatomy, and to support or repair a specific tissue or type of tissue. Exemplary dimensions can be sufficient to allow the tissue support portion to contact tissue to be repaired or supported, and to allow extension portions to extend from the tissue support portion to a desired anatomical location to allow the extension portion be secured to anatomy of the pelvic region (e.g., supportive tissue), to support the tissue support portion.

Dimensions of extension portions can allow an extension portion to reach between a tissue support portion placed to support pelvic tissue (at an end of the extension portion connected to the tissue support portion) and a location at which the distal end of the extension portion attaches to pelvic tissue (e.g., supportive tissue). A distal end of an extension portion can include a self-fixating tip that can be attached directly to pelvic tissue such as pelvic muscle, ligament, or tendon, bone, or other supportive tissue. The length of the extension portion, therefore, can be in a range that allows placement of a tissue support portion as desired to support pelvic tissue, while the self-fixating tip is placed in pelvic tissue such as supportive tissue.

A length of an extension portion can optionally be fixed (i.e., the extension portion need not include, and according to certain embodiments may specifically exclude, any form of length-adjusting mechanism), as can a length of an implant spanning from opposite self-fixating tips and including extension portions and a length or segment of tissue support portion. Alternate implants may include adjustment or tensioning mechanisms that allow a physician to alter the length of an extension portion before, during, or after implantation. See, e.g., International application number PCT/US2007/014120, filed Jun. 15, 2007, by Dockendorf et al., titled "SURGICAL IMPLANTS, TOOLS, AND METHODS FOR TREATING PELVIC CONDITIONS"; and International application number PCT/US2011/025917, filed Feb. 23, 2011, by Wirbisky et al., titled "SURGICAL ARTICLES AND METHODS."

Alternately, adjustment and tensioning mechanisms can also be excluded from embodiments of implants of the invention by selecting the length of extension portions and tissue support portion, and by adjusting for tensioning or positioning of extension portions and tissue support portions based on placement of the self-fixating tip within the pelvic tissue, selected placement including selection of the point of insertion of a self-fixating tip and depth of insertion of the self-fixating tip.

An extension portion of an implant can include an anchor (e.g., self-fixating tip) at an end of the extension portion that is distal from a tissue support portion. The anchor in general can be a structure connected to a distal end of an extension portion and that can be implanted into supportive tissue in a manner that will maintain the position of the anchor and the attached implant. Optionally, a self-fixating tip can also be designed to engage a distal end of an insertion tool so the insertion tool can be used to push the self-fixating tip into supportive tissue for implantation, then optionally adjust the placement. The anchor may engage the insertion tool at an internal channel within a base of the anchor, at a location external to a base, or at a lateral extension, as desired.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA, and the like.

A self-fixating tip also, preferably, includes one or more lateral extension that can increase the force required to remove the self-fixating tip from supportive tissue after insertion into the tissue, i.e. the "pullout force." At the same time, a lateral extension can be designed to exhibit a reduced or relatively low "insertion force," which is the amount of force used to insert the self-fixating tip into tissue.

Exemplary self-fixating tips described herein include a cylindrical base or tapered cylindrical base, with a hollow or solid interior. Other shapes for a base may also be useful, such as blocks having square or rectangular forms when viewed in cross section along a longitudinal axis extending from a proximal base end to a distal base end. For those types of self-fixating tips, dimensions of a square or rectangular cross section can be of a range similar to the described range of diameters of a cylindrical base, such as from about 2 to about 5 millimeters in either dimension when viewed in cross section.

As examples of specific ranges of lengths of exemplary self-fixating tips, lengths (measured from the proximal base end to the distal base end along a longitudinal axis of the self-fixating tip) in the range from 0.4 to 1.0 centimeter, e.g., from 0.4 to 0.8 centimeters, or from 0.4 to 0.7 centimeters, have been found to be useful. These ranges are specifically useful for self-fixating tips that can be inserted into tissue of the obturator internus, because the relatively short length can allow the self-fixating tip to be inserted into the muscle tissue a desired depth, i.e., over a range of depths, optionally without penetrating the obturator membrane. More generally, the self-fixating tip can be of a length dimension that is less than the thickness of muscle or other supportive (pelvic) tissue into which the self-fixating tip is to be inserted, so the self-fixating tip can be inserted a desired distance into the tissue.

A lateral extension can be rigid or "fixed" relative to a base so the lateral extension does not substantially move or deflect during or after implantation. For example, a fixed lateral extension can be a lateral extension that is not substantially moveable relative to the base in a manner that certain types of known soft tissue anchor extensions are moveable, for instance between a non-deployed or non-extended position that places an extension against the base to allow insertion of the anchor into tissue with a reduced size or shape profile, and a deployed or extended position that places the extension away from the base to engage tissue and prevent movement of the self-fixating tip in a direction opposite of the direction of insertion.

Alternate embodiments of lateral extensions can be moveable or deflectable, if desired, such as to allow a reduced insertion profile, and insertion force, and to allow placement of an anchor within a tunneler tool. A lateral extension may deflect backward (toward the proximal base end or against the base) when a self-fixating tip is being pushed through a tunneler tool, or through tissue. Upon exiting the tunneler tool and upon entry into tissue, the moveable lateral extension may extend away from the base to produce a larger cross-sectional profile of the self-fixating tip, and increase pullout force.

A self-fixating tip can be connected to an extension portion of an implant in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006/0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form an anchor (e.g., self-fixating tip)at an end of an extension portion. The anchor (e.g., self-fixating tip) can be as described herein, for example, including lateral extensions and an internal channel.

Figure 1B:
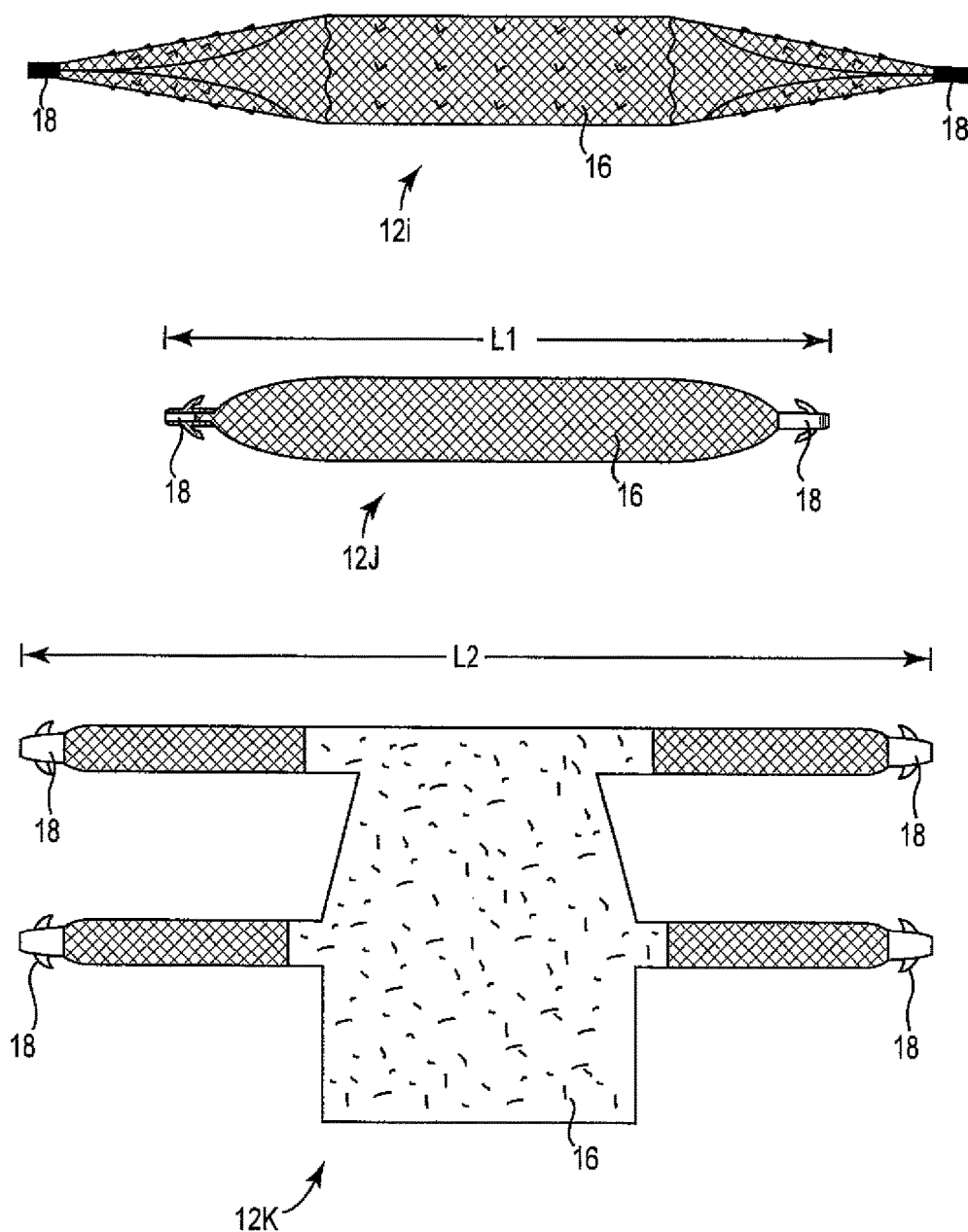

Referring to FIGS. 1A and 1B, portions of exemplary implant embodiments (12) are shown, 12a through 12k. Each of implants 12a through 12k includes a support portion, one or two extension portions, and one or multiple tissue fixation devices such as a soft tissue anchor or self-fixating tip 18. Each implant 12a through 12k includes a mesh (or biologic) portion 16 that includes the support portion (boundaries of which are not specifically demarcated), and one or two extension portions that each include one or more anchor or anchors (e.g., self-fixating tip) 18. As illustrated 12a through 12f, an extension portion can include a non-mesh elongate structure such as a suture, filament, polymeric rod, or other non-mesh elongate extension upon which one or more anchor 18 can be located, at a location along a length of the extension portion or at an end of the extension portion distal from the support portion. Alternate embodiments of implants can include extension portions made of another material such as a mesh other film or porous material, or a biologic material. See implants 12g through 12k.

Illustrated implants 12a through 12k include a mesh portion 16 (support portion 16 of implant 12k is illustrated as cadaveric but may alternately be mesh) and one or more anchors 18 provided at an end of an extension portion of implant 12. As illustrated, mesh portion 16 and anchors 18 are adapted for insertion and anchoring within a pelvic anatomy of a patient to treat urinary incontinence in a male or female (also optionally female vaginal prolapse, as with FIG. 12k) by supporting tissue of the patient's bladder, bladder neck, urethra or like tissue structure.

Each anchor 18 can be of any design, e.g., having features as specified for a self-fixating tip as described herein. An anchor located at a distal end or along a length of an extension portion can be adapted to engage and be pushed by an insertion tool, and can include multiple lateral extensions that can be either extendable or fixed relative to a base of the anchor. According to certain specific embodiments, an anchor can optionally serve as a plug that closely fits a distal end opening of a tunneler tool.

Referring to implant 12*a*, the illustration shows one anchor, 18, e.g., a self-fixating tip, at an end of the illustrated extension portion distal from the support portion. The anchor can be of any design and may include a base, an internal channel extending longitudinally from the proximal base end for engaging an insertion tool, and one or multiple lateral extensions, which may be fixed or extendable. Anchor 18 can fit within an open internal channel of a shaft of a tunneler tool, and preferably can be inserted at a proximal end of a tunneler tool shaft and advanced to a distal end of the tunneler tool shaft by pushing anchor 18 at a distal end of an insertion tool. As illustrated, anchor 18 is in the form of one pointed, "dart"-style soft tissue anchor or self-fixating tip. A proximal end of a base of anchor 18, as illustrated, can engage a distal end of a shaft of an insertion tool to allow the insertion tool to push anchor 18.

Implant 12*b* includes features of implant 12*a*, including features of anchor 18, but differs in that implant 12*b* includes multiple anchors 18 along a length of an extension portion of implant 12.

Implants 12*c* and 12*d* include features of implants 12*a* and 12*b*, including certain features of anchor 18, but with certain differences in anchor shape. Implant 12*c* includes multiple anchors 18 placed along a length of an extension portion of implant 12*c*. Each anchor includes a circular cross-section when viewed from a side, or a spherical shape. Each anchor 18 can fit within an open internal channel of a shaft of a tunneler tool, and preferably can be inserted at a proximal end of a tunneler tool shaft and advanced to a distal end of the tunneler tool shaft by pushing anchor 18 at a distal end of an insertion tool. Optionally, the most distal anchor can be useful as a plug to fill a distal end opening of a tunneler tool, when placed at a distal end of an insertion tool. Each anchor 18 may have one or more fixed or extendable lateral extensions. Each anchor may optionally be radiopaque.

Implant 12*d* is similar to implant 12*c*, but anchors 18 of implant 12*d* have a rectangular or square profile when viewed from a side (as illustrated). A longitudinal cross section (not shown) of anchors 18 may be an useful shape adapted to fit within an open internal channel of a shaft of a tunneler tool, e.g.: square, rectangular, circular, hexagonal, octagonal.

Implants 12*e* and 12*f* include anchors 18 as identified for FIGS. 12*c* and 12*d*, respectively, but each only includes a single anchor at an end of the extension portion distal from the support portion of the implant.

Implants 12*g* and 12*h* include a support portion and extension portion made of a single, integral mesh material 16. Implant 12*g* includes multiple anchors 18 (of any specific or general design described herein), along a length of an extension portion. Implant 12*h* includes a single anchor 18 (of any specific or general design described herein), at an end of an extension portion distal from a support portion.

Implant 12*i* includes a mesh support portion and two mesh extension portions. Each mesh extension portion is in the form of a mesh tube or wound (when viewed along the longitudinal axis of the implant) mesh. Each anchor 18 can be secured to a mesh extension portion by bonding an inner surface of the wound mesh extension portion to an outer surface of each anchor 18, by injection molding, or by any other useful securing mechanism.

Implant 12*j* can be useful for treating urinary incontinence in a male or female patient. Implant 12*j* has a support portion, two extension portions, and two self-fixating tips, one at an end of each extension portion. Implant 12*k* can be useful for treating anterior female vaginal prolapse such as cystocele, along with urinary incontinence. Implant 12*k* has a support portion, two superior extension portions, two inferior extension portions, and four self-fixating tips, one at an end of each extension portion. At least two of the extension portions can be placed (via a transvaginal incision) at a patient's opposing obturator foramen with the support portion being placed in contact with anterior tissue of a vagina, or to support a urethra, bladder, or bladder neck. The lengths (L1 and L2) of implants 12*j* and 12*k* between distal ends of extension portions can be sufficient to place opposing self-fixating tips at positions and depths of tissue of the obturator foramen, preferably without penetrating the obturator membrane, with the implant reaching between the opposing obturator foramen while supporting urethra or vaginal tissue. Exemplary lengths of an implant or implant portion for extension below the urethra, between opposing obturator foramen, from distal end to distal end of the extensions while laying flat, can be in the range from about 6 to 15 centimeters, e.g., from 7 to 10 centimeters or from 8 to 9 centimeters or about 8.5 centimeters. (Lengths L1 and L2 of implants 12*j* and 12*k* can be within these ranges.) The lengths are for male and female urethral slings, and are for anterior portions of implants for treating female anterior prolapse or combined female prolapse and incontinence, which include an anterior portion that has a length between ends of anterior extensions portions within these same ranges. A width of the extension portion can be as desired, such as within the range from about 1 to 1.5 centimeters.

A tunneler tool or insertion tool can include a rigid elongate shaft that includes a distal end, a proximal end, an open internal channel, a proximal end opening in communication with the open internal channel, and a distal end opening in communication with the open internal channel. According to certain embodiments, the shaft can include a longitudinal opening along a length of the shaft, either along an entire length or a portion of the length that include a portion of length at the distal end of the shaft.

The shaft can be made of a hollow tube comprising or consisting of a narrow sidewall, optionally including a longitudinal opening (e.g., slot or channel) extending from the proximal end to the distal end, optionally from the proximal end opening to the distal end opening. The shaft can be elongate and straight or curved in two or three dimensions, and can be considered to include a straight or curved longitudinal axis extending lengthwise and tangentially through a center of the shaft when viewed in cross section. The cross section of the shaft may be uniform along the length, or non-uniform, and may be circular or optionally non-circular (e.g., oval, square, rectangular, angled, cornered, etc.). The proximal end of the shaft may optionally connect to a handle. The distal end, at the terminus of the distal end (e.g., the distal end tip), can include a distal end opening (in cross section) in communication with the open internal channel and optionally in connection with the optional longitudinal opening. A distal end terminus can also include an angled or beveled end that defines a plane or surface that is not orthogonal to a longitudinal axis extending through the shaft at the distal end tip.

Figure 2:
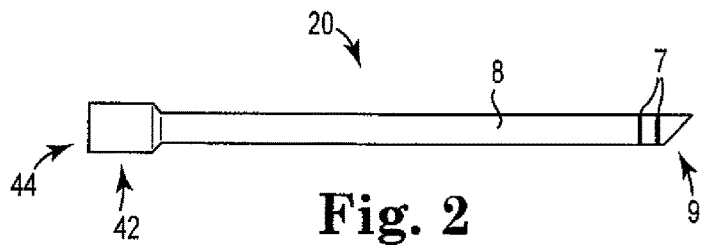
FIG. 2 illustrates an exemplary tunneler tool as described.

As shown at FIG. 2, tunneler tool 20 can include a straight (alternately curved) shaft 8 extending from a proximal end adjacent to handle 42, to a distal end that includes distal end tip 9. Shaft 8 is hollow (i.e., includes an open internal channel) to allow passage through shaft 8 of a component of an implant along with an insertion tool. Shaft 8 includes a proximal end opening 44 at the proximal end of the shaft, in communication with the open internal channel, and a distal end opening at the distal end of the shaft, also in communication with the open internal channel. The longitudinal opening along a portion or the entire length of shaft 8 can be useful to allow lateral separation of the tunneler tool and an insertion tool (or distal portion thereof) contained therein. Optional markers 7 at the distal end of shaft 8 are radiopaque markers. Alternately, the entire shaft 8 may be radiopaque.

Figure 3:
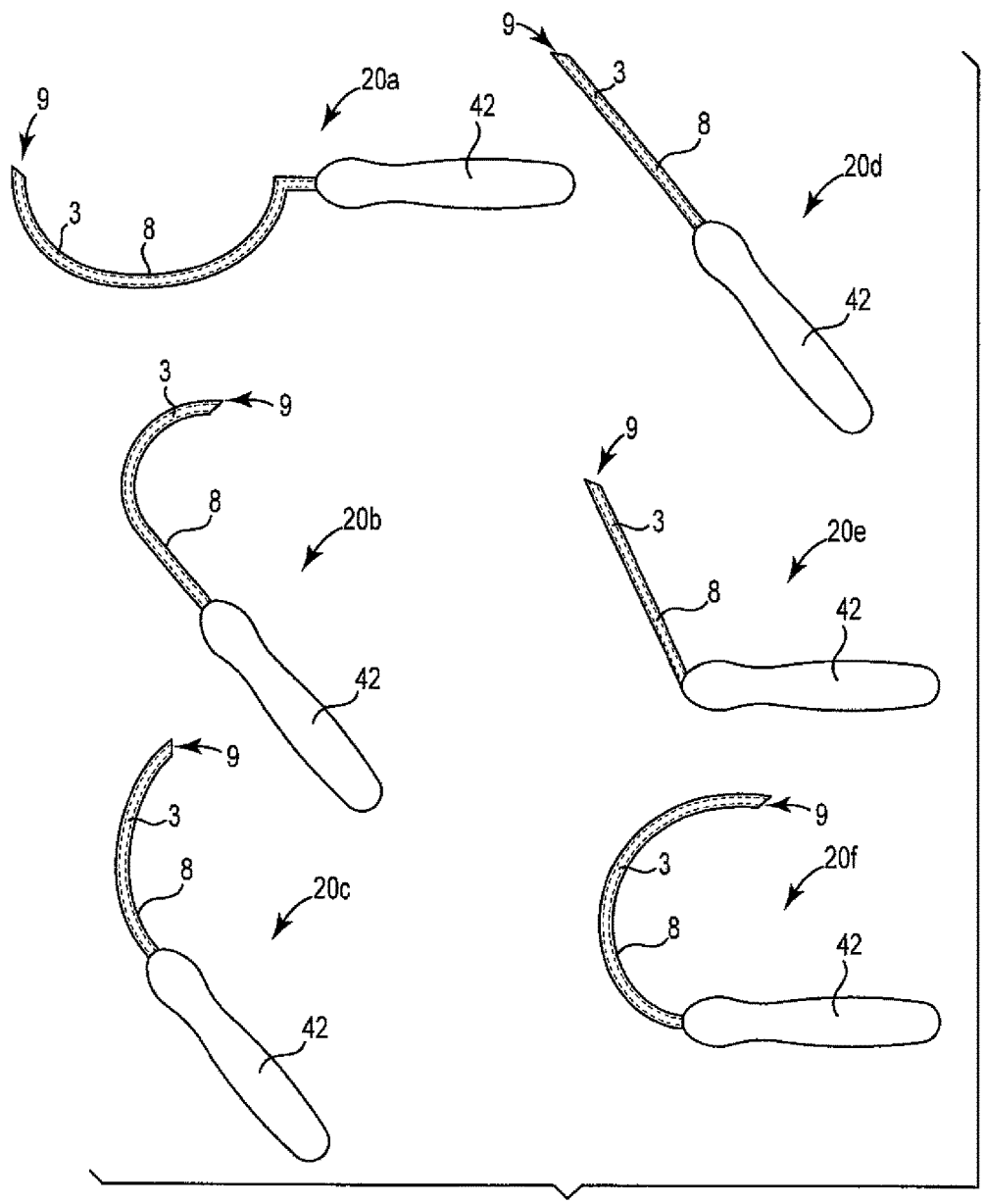
FIG. 3 illustrates exemplary tunneler tools as described.
Figure 4A:
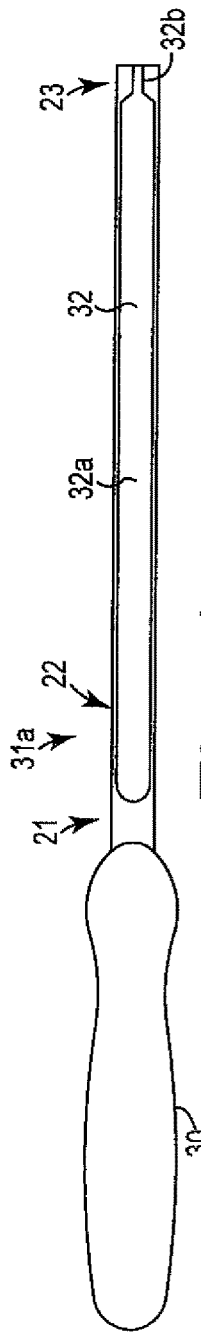
FIGS. 4A and 4B (top view and side view, respectively), 4C and 4D (top view and side view, respectively), 4E and 4F (top view and side view, respectively), and 4G and 4H (top view and side view, respectively), illustrate examples of insertion tools as described.
Figure 4B:
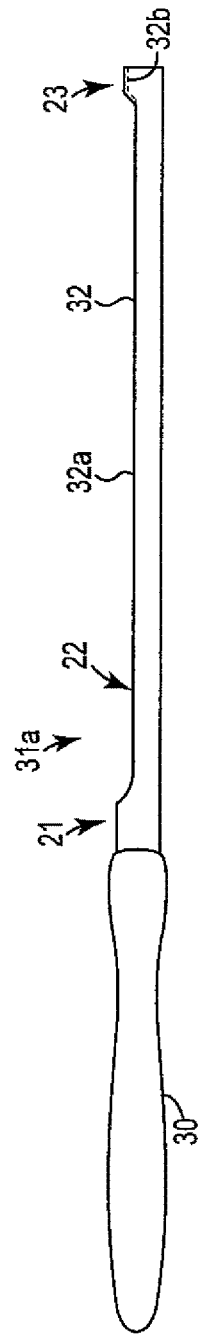
Figure 4C:
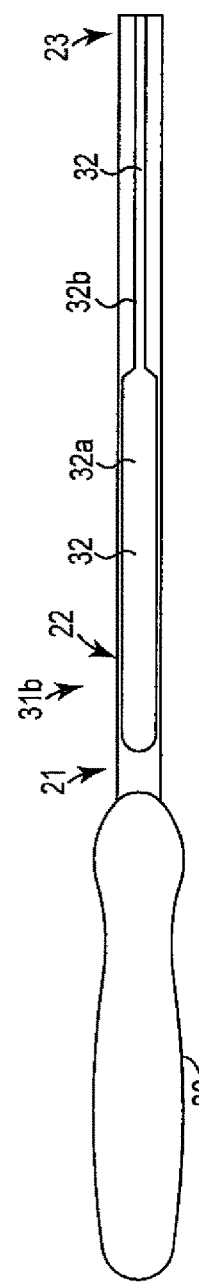
Figure 4D:
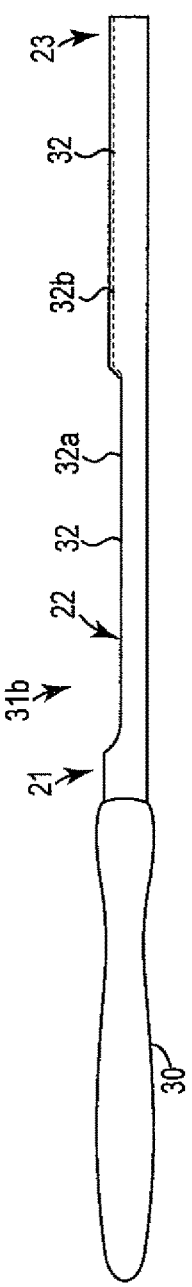

FIG. 3 shows alternate tunneler tools 20*a* through 20*f*, each including a handle 42 and elongate shaft 8 having an internal open channel (not shown). Distal end tip 9 can be beveled, as illustrated. As shown, a tunneler tool shaft 8 and handle 42 may be configured according to any of various designs, including: a straight shaft 8 and a straight handle 42 aligned together along a longitudinal axis (tool 20*d*), a straight shaft 8 and a straight handle 42 connected at a corner (tool 20*e*), a shaft 8 having a single radius curve (tool 20*c* or 20*f*) or a multi-radius curve (tool 20*b*), or a tool having a proximal straight shaft portion connected to a distal curved shaft portion, and straight handle aligned along a longitudinal axis with the proximal straight shaft portion (tool 10*a*). Various other shapes and sizes can also be employed without deviating from the spirit and scope of the present invention. Each of tunneler tools 20*a* through 20*f* includes a proximal end opening (44, not specifically illustrated) on shaft 8. The proximal end opening can be at any useful location of each tunneler tool, e.g., at a proximal end of shaft 8, and may extend into handle 42 (also not illustrated).

A system as described can also include an optional removable core tool adapted to fit within an open internal channel of a tunneler tool, to fit, fill, or plug the distal end opening during use of the tunneler tool to create a path through tissue (a tissue path). A core tool may completely fill the open internal channel of the tunneler tool, and may optionally include a bearing on a proximal end to engage the tunneler tool at the proximal end opening, to allow the proximal end of the core tool to be used to push the tunneler tool. A proximal end of the core tool may also include a handle.

During insertion of a tunneler tool, the distal end tip of the tunneler tool, including the distal end opening, will be pressed against, into, and through intact tissue of a patient to create an open tissue path. To prevent undue trauma to the tissue during the creation of the tissue path, a distal end opening of the tunneler tool can be plugged by a removable core tool or other structure such as a distal end of an inserter tool or anchor. For example, a core tool can be inserted through a proximal end opening of a shaft of a tunneler tool, to advance a distal end of the core tool to reach and plug and closely match the space, size, and shape of the distal end opening of the tunneler tool. The distal end of the core tool is adapted to fit closely to the size and shape of the distal end opening, i.e., to plug the opening, so when the distal end of the core tool is placed within the distal end opening of the tunneler tool, the distal end of the core tool will plug or fill the distal end opening and inhibit or prevent the distal end opening from cutting tissue. With the core tool (or another structure, as mentioned) installed in the tunneler tool to plug the open distal end, the tunneler tool can be used to create a tissue path in a patient without causing undue tissue trauma. After the tissue path is created, the core tool (or other structure) can be removed by withdrawing the core tool (or other structure) from the proximal end of the shaft of the tunneler tool in a proximal direction. The shaft of the core tool can be rigid or flexible, and either straight or curved, to allow the shaft of the core tool to adapt to a straight or curved open internal channel of the tunneler tool.

An insertion tool can be used to pass an implant or a portion of an implant (e.g., extension portion, self-fixating tip, or the like) through a tunneler tool to a distal end of the tunneler tool shaft and to a location at which the implant will be secured to tissue of a patient. Various types of insertion tools are known, and these types of tools and modifications thereof can be used according to the present description.

Certain embodiments of insertion tools can include a relatively flexible shaft having an asymmetrical cross section, or asymmetrical indexers. Such a tool may be useful with a tunneler tool that is straight or curved, that include an open internal channel that may or may not have an asymmetrical cross section, and that includes a longitudinal opening along the full length of the tunneler tool shaft. The insertion tool may be inserted into the open internal channel at one rotation, to match a cross-section of the open internal channel, allowing the asymmetrical shaft to be advanced along an optionally curved open internal channel without becoming displaced through the longitudinal opening. When contained within the open internal channel, the asymmetrical shaft can be turned and oriented (e.g., rotated, e.g., approximately ninety degrees) to allow the tunneler tool to be removed from (slid off of) the insertion tool by moving the tunneler tool laterally; a narrow dimension of the insertion tool shaft (or one or more indexer located on the shaft) can be aligned with the longitudinal opening of the tunneler tool, allowing the shaft (or one or more indexer) to pass through the longitudinal opening.

Certain embodiments of useful insertion tools include those types of tools that generally includes a shaft (e.g., a thin elongate, rigid needle) that attaches at a proximal end to a handle; a handle attached to one end (a proximal end) of the shaft; and a distal end of the shaft adapted to engage a self-fixating tip (or other engagement) of an implant to allow the insertion tool shaft to push the self-fixating tip through a tunneler tool and insert the self-fixating tip within tissue of a patient's pelvic region. This class of tool can be used with a self-fixating tip that includes an internal channel designed to be engaged by a distal end of an insertion tool. Other general types of insertion tools will also be useful, but may engage a self-fixating tip in a manner that does not involve an internal channel of a self-fixating tip. For example, alternate insertion tools may include a relatively larger shaft (in cross-section). See, for example, systems as illustrated at FIGS. 6B, 6C, 6D, 6E, and 7.

Exemplary insertion tools for treatment of incontinence and vaginal prolapse are described, e.g., in U.S. patent application Ser. Nos. 10/834,943, 10/306,179; 11/347,553; 11/398,368; 10/840,646; United States patent publication numbers 2010/0256442; 2011/0034759; PCT application numbers 2006/028828; 2006/0260618; and PCT Publication No. WO 2011/106419; among others. Tools described in those patent documents are designed for placement of an implant in a pelvic region for the treatment of prolapse, male or female incontinence, etc. The insertion tools of the above-referenced patent documents and for use as described herein may include a shaft (e.g., metal or polymeric needle) that is rigid and curved in two or three dimensions and that can extend through a medial incision in a male or female (e.g., a perineal incision or a vaginal incision, respectively), laterally past a urethra, and to an obturator foramen. A length of a straight or curved insertion tool shaft can be sufficient to reach from a medial (vaginal or perirectal) incision to an obturator foramen, for example. Alternately, for placing an end of an implant at a location other than an obturator foramen, the length of the insertion tool shaft may be sufficient to reach from a medial (vaginal or perirectal)

incision to a different muscle or tissue (supportive tissue) such as a levator ani, coccygeous muscle, iliococcygeous muscle, arcus tendineus, sacrospinous ligament, etc., to place a self-fixating tip at one of those supportive tissues.

Exemplary insertion tools for use according to this description can be similar to or can include features of tools described in the above-referenced patent documents. For use according to methods described herein, those insertion tools may be modified to allow the insertion tool to be used to place an implant or portion of an implant (e.g., an extension portion or a self-fixating tip) through a tunneler tool, and then allow the tunneler tool and the shaft of the insertion tool be separated (inside of the patient), such as by moving the tunneler tool laterally such that the insertion tool shaft passes through a longitudinal channel located along a length of the tunneler tool shaft, e.g., at a distal end of the tunneler tool shaft or along a length between the distal end and the proximal end of the tunneler tool shaft.

FIGS. 4A, 4C, 4E, and 4G (top view) and 4B, 4D, 4F, and 4H (side view) show examples of insertion tools 31a through 31d having handle 30 at a proximal end of tool 31, a shaft 22 having a distal end 23 and a proximal end 21 (attached to handle 30). Each distal end 23 includes a distal end tip adapted to engage a portion of an implant, to use the distal end tip to advance the portion of implant through an open internal channel of a shaft of a tunneler tool. According to these embodiments, a tunneler tool can be used to create a tissue passage in a patient, an insertion tool can engage an implant or a portion of the implant, and the insertion tool and attached implant or portion of implant can be inserted into the tunneler tool at a proximal end of the tunneler tool shaft. The assembly of the insertion tool and attached implant or implant portion can then be advanced along the length of the tunneler tool shaft, within the open internal channel, to the distal end of the tunneler tool shaft. The implant and the insertion tool shaft (e.g., 22) can fit together within the open internal channel of the tunneler tool, with the implant being held against the insertion tool shaft to fit against or within the recessed region 32.

A shaft 22 of insertion tool 31, as illustrated, may be straight or curved, and can preferably be rigid. As illustrated at FIGS. 4A through 4H, each shaft includes a recessed region 32 or space adapted to fit an implant or a portion of implant. For example, shaft 22 of insertion tool 31a is relatively straight, substantially rigid (e.g., stainless steel), and includes recessed region 32 extending along one side of shaft 22. Recessed region 32 includes a relatively wider portion (32a) along a major length of shaft 22 that is adapted to engage a mesh or similar extension portion of an implant. Recessed region 32 also includes a relatively narrow portion (32b) located at or near the distal end tip of shaft 22, adapted to engage a portion of an implant that has relatively smaller dimensions such as an elongate suture or similar structure.

Shaft 22 and recessed region 32 of insertion tool 31b are similar to those of insertion tool 32a, other than different relative sizes, lengths, and locations, of the wider and narrower portions 32a and 32b of recessed region 32. Insertion tool 31b may be adapted for use with one or more of implants 12a, 12e, and 12f of FIGS. 1A and 1B, for example.

Shaft 22 and recessed region 32 of insertion tool 31c are somewhat similar to those of insertion tool 31b, other than multiple larger recessed regions 32c extending along a length of narrower portion 32c. Insertion tool 31c may be adapted for use with one or more of implants 12b, 12c, and 12d of FIGS. 1A and 1B, for example.

Shaft 22 and recessed region 32 of insertion tool 31d are somewhat similar to those of insertion tool 31a, or may alternately be similar to those of insertion tool 31b or 31c. Shaft 22 of tool 31d includes a curved proximal portion and a straight distal portion. Curved shaft 22 of insertion tool 31d may be substantially rigid (e.g., made of stainless steel, rigid plastic or polymer, or a comparable material), and when used in combination with a rigid tunneler tool, can include a distal straight portion that is of sufficient length to match a straight length of a straight elongate opening of a distal portion of a tunneler tool. That is, the distal straight portion of shaft 22 can preferable be at least as long as a straight distal portion of a tunneler tool shaft.

Figure 5A:
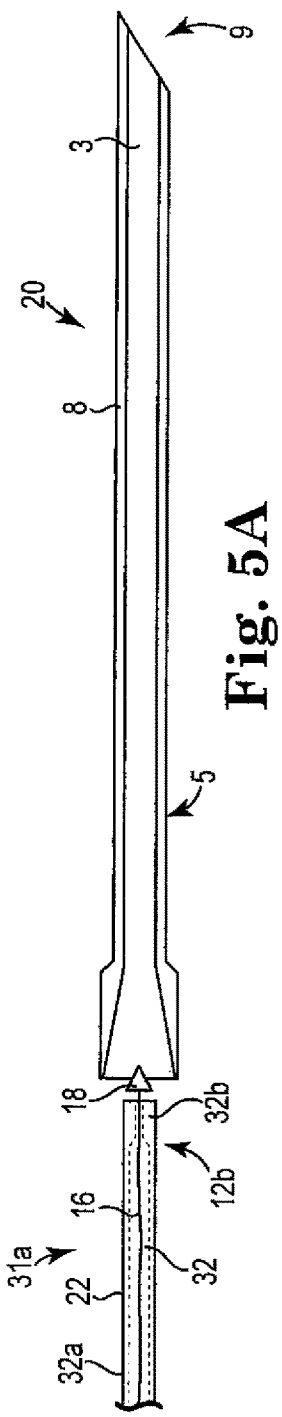
FIG. 5A illustrates a system as described, including a distal end of an insertion tool (top view), and a tunneler tool (in cross section).
Figure 5B:
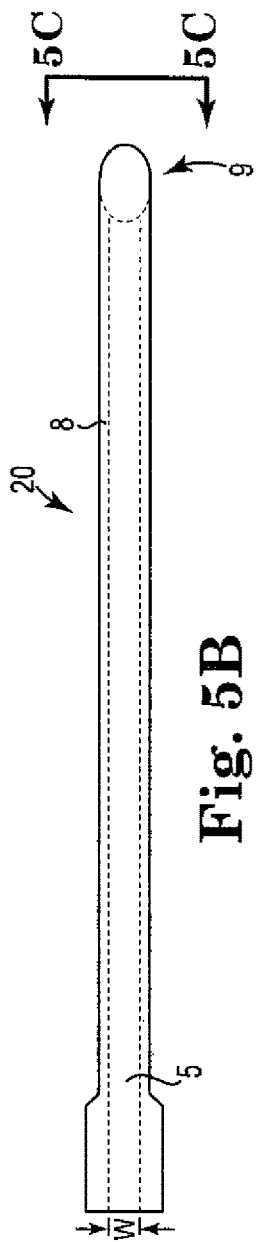
FIG. 5B illustrates a top view of the tunneler tool of FIG. 5A.
Figure 5C:
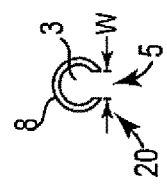
FIG. 5C illustrates an end view of the tunneler tool of FIG. 5B.

FIGS. 5A (cross-sectional view), 5B (top view), and 5C (end view) show insertion tool shaft 22 of insertion tool 31a of FIG. 1A, with implant 12b engaged along a length at a distal portion of shaft 22, and positioned against recessed region 32. FIG. 5A is a cross-sectional view of a tunneler tool 20, having handle 42 at a proximal end, and a beveled distal end tip 9. The side view at FIG. 5A also shows open internal channel 3 of tunneler tool 20. The top view at FIG. 5B shows shaft 8 and longitudinal opening 5 represented by dashed lines. The end view at FIG. 5C shows open internal channel 3 and longitudinal opening 5. FIG. 5C also denotes a dimension (width) of longitudinal opening 5; an insertion tool shaft 22 can be passed through longitudinal opening 5 if the shaft has a cross-sectional dimension that is smaller than the width (w) of longitudinal opening 5.

Generally, an implant (12) as described herein can be used in combination with a tunneler tool 20 and an insertion tool 31. The implant 12 can include the anchor 18 adapted as an end cap for communication with and guidance by the insertion tool 31. The insertion tool 31 can take on the form of a push rod to pass through a tunneler tool 20, and can be constructed of various metal or polymer materials known to those of ordinary skill in the art. A shaft 22 can be straight, curved, and substantially rigid, and can include a distal end that engages an implant, such as anchor or self-fixating tip of an implant. Optionally, a shaft 22 of insertion tool 31 can include a bend, corner, or other features to facilitate guidance and use in conjunction with an implant and tunneler tool 20. For instance, a bend can permit maneuvering of the shaft 22 through an elongate opening (slot) 5 of a tunneler tool 20. See FIGS. 16B, 17, 18A through 18C, 21, and 22. Other embodiments of an insertion tool 31, as shown in FIG. 8E, can include a cutting blade 50 or device incorporated for use during deployment. The cutting blade 50 can be fixed, selectively deployable/retractable or otherwise provided to facilitate its use.

Figure 6A:
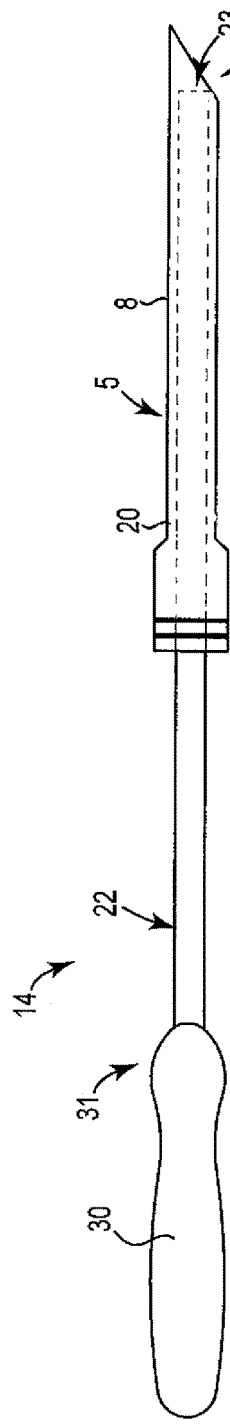
FIG. 6A illustrates a side view of a system as described, including an insertion tool and a tunneler tool.

Referring to FIG. 6A, an embodiment of a delivery tool system 14 is illustrated to include insertion tool 31 having handle 30 and shaft 22, and tunneler tool 20 having shaft 8, distal end tip 9, open internal channel 3 extending between a proximal shaft end and a distal shaft end, and a longitudinal opening 5 extending along a length of shaft 8. An implant (not shown) can be engaged at a distal end 23 of shaft 22 and inserted into open internal channel 3 of tunneler tool 20. In use, a plug (e.g., as part of a tissue anchor or as a distal end of a core tool or insertion tool) can be placed at a distal end opening of shaft 8, and tunneler tool 20 can be used to create a tissue path in a patient. A core tool, if used, or the insertion tool, can then be removed from tunneler tool 20. A distal end 23 of insertion tool 31 can then be placed in engagement with an implant (or portion thereof) and the insertion tool can be used to pass the implant (or portion thereof) through the open internal channel 3 of tunneler tool 20.

Figure 6B:
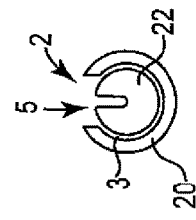
FIGS. 6B and 6C are end view illustrations of alternate embodiments of a tunneler tool and insertion tool of FIG. 6A.

FIG. 6B shows an example of a cross-sectional or end view of features of a delivery tool system 14 such as that shown at FIG. 6A. In particular, shaft 22 can have a non-circular cross-section (shape and dimension) with opposed flat sides and radiused ends (in cross section) that, when properly oriented within open internal channel 3 allows shaft 22 to be disengaged with (i.e., removed from) open internal channel 3, by shaft 22 passing through longitudinal opening 5.

Figure 6C:
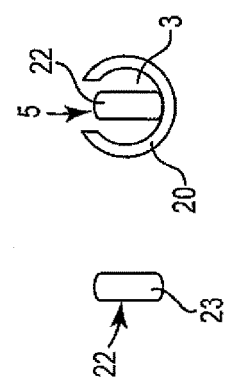

FIG. 6C shows another example of a cross-sectional or end view of features of a delivery tool system such as that shown at FIG. 6A. In particular, shaft 22 can have a non-circular cross section (shape and dimension) including notch 2. When shaft 22 is twisted, notch 2 can engage an edge or lip of a wall of shaft of 8 of tunneler tool 20 at longitudinal opening 5, and shaft 22 can be removed from open internal channel 3 by twisting shaft 22, and moving shaft 22 through longitudinal opening 5.

Figure 6D:
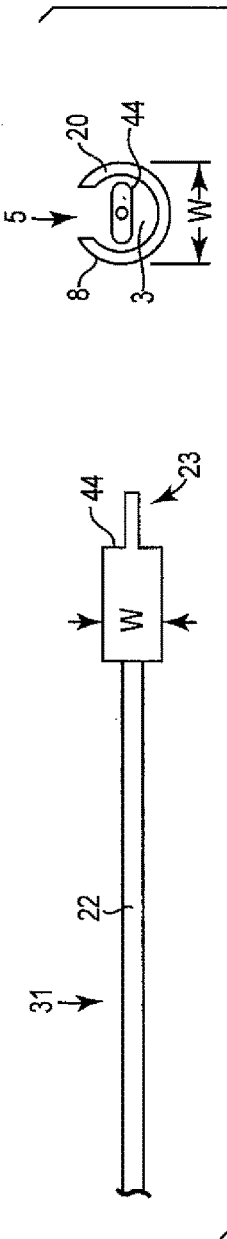
FIG. 6D illustrates a side view and an end view of an alternate embodiment of tunneler tool and insertion tool of FIG. 6A.

FIG. 6D shows another example of features of a delivery tool system such as that shown at FIG. 6A. In particular, in the side view, shaft 22 of insertion tool 31 can be seen to have a narrow proximal portion and a widened indexing feature (or "indexer") 44 toward a distal end of shaft 22. Indexing feature 44 extends laterally relative to the narrow portion of shaft 22 (see end view). Also in this embodiment, shaft 8 and open internal channel 3 of tunneler tool 20 can include a non-circular cross section with a width dimension (w) adapted to provide a close fit with the width of indexing feature 44. With insertion tool 31 inserted into tunneler tool 20, the width (w) of indexing feature 44 causes insertion tool 31 to become oriented with the width of indexing feature 44 aligned with a width dimension (w) of tunneler tool 20. When shaft 22 is rotated ninety degrees, indexing feature 44 can align with longitudinal opening 5 and shaft 22 with indexing feature 44 can be removed from open internal channel 3 of tunneler tool 20 by moving shaft 22 laterally through longitudinal opening 5.

Figure 6E:
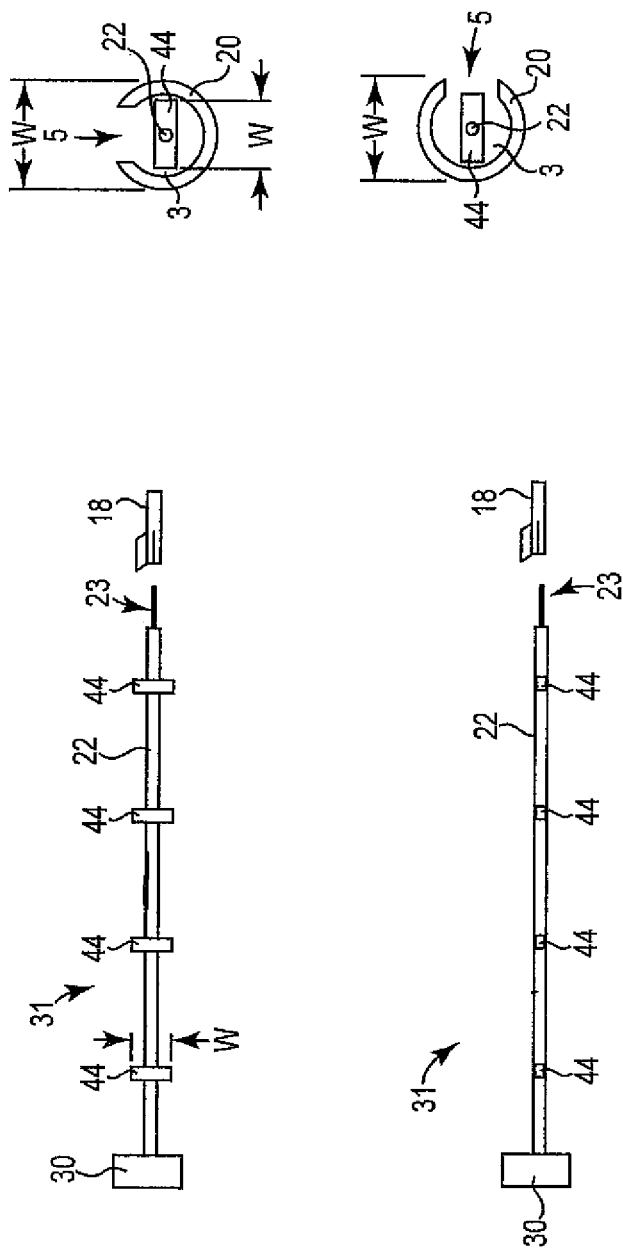
FIG. 6E illustrates a side view and an end view of an alternate embodiment of tunneler tool and insertion tool of FIG. 6A.

FIG. 6E shows another example of a delivery tool system such as that shown at FIG. 6D, and including multiple indexing features 44. In the side view, shaft 22 of insertion tool 31 can be seen to include narrow extending shaft 22 and multiple indexing features 44 located at intervals along the length of shaft 22. Indexing features 44 extend laterally relative to shaft 22 (see end views). Also in this embodiment, shaft 8 and open internal channel 3 of tunneler tool 20 can include a non-circular cross section with a width dimension (w) adapted to provide a close fit with indexing feature 44 (see end views). With insertion tool 31 inserted into tunneler tool 20, the extended width (w) of indexing feature 44 causes insertion tool 31 to become oriented with the width of indexing feature 44 aligned with a width dimension (w) of tunneler tool 20. When shaft 22 is rotated ninety degrees (see side view rotated ninety degrees and end view rotated ninety degrees), indexing features 44 can align with longitudinal opening 5, and shaft 22 with indexing feature 44 can be removed from open internal channel 3 of tunneler tool 20 by moving shaft 22 laterally through longitudinal opening 5 (see end view rotated ninety degrees).

Referring to FIG. 6F, illustrated is an embodiment of insertion tool 31 for use as part of a delivery tool system described herein, in conjunction with an implant and a tunneler tool 20 as also described. As illustrated, in addition to other features described herein for use in an insertion tool 31, the illustrated insertion tool 31 can optionally also include a cutting blade 50 or device incorporated at distal end 23, which can also be useful to engage an anchor 18, such as a self-fixating tip. Cutting blade 50 can be fixed, selectively deployable and retractable, or otherwise provided to facilitate use during a surgical procedure. At FIG. 6F, insertion tool 31 is configured with a retracted cutting blade 50 at the upper illustration, and is configured with an extended cutting blade 50 at the lower illustration.

Figure 7:
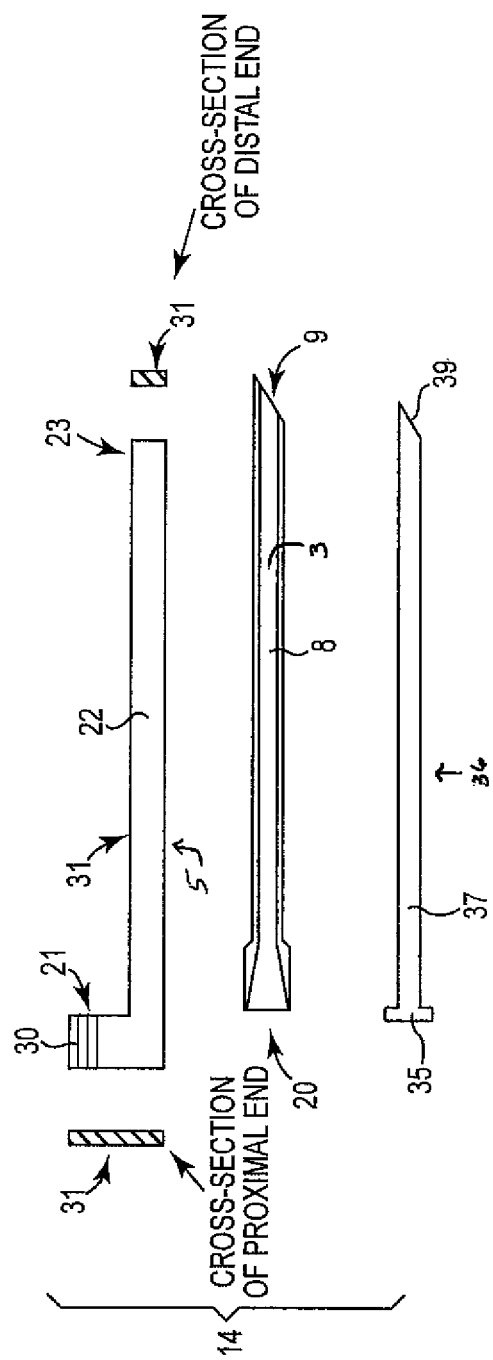
FIG. 7 illustrates an exemplary system as described including an insertion tool (including cross sectional or end views of a proximal end and a distal end), a tunneler tool (in cross section), and a core tool (side view).

As shown at FIG. 7, a delivery system 14 can include a multi-component assembly comprising a tunneler tool (or stylet) 20, an optional core tool 36, and an insertion tool 31. Tunneler tool 20 is adapted for receiving at least a portion, such as an end portion, of insertion tool (pusher tool) 31 (and also at least a portion, such as an end portion, of core tool 36).

In use, systems shown at FIGS. 6B through 6E, and 7, can be used by making an incision and inserting the tunneler tool into the incision, while a core tool or insertion tool is contained in the open inner channel, and a distal end of the core tool or insertion tool plugs and blocks the distal end opening of the tunneler tool. The assembly of the tunneler tool and core tool or insertion tool can be advanced through the incision and through tissue to place a distal end of the tunneler tool at a region of supportive tissue on one side of a patient. Plugging the distal open end prevents the open distal end of the tunneler tool from cutting a plug of tissue or otherwise producing undue trauma. After insertion of the assembly of the tunneler tool and the core tool or insertion tool, the core tool or insertion tool can be removed to expose and open the lumen (open internal channel) of the tunneler tool. A distal end of the insertion tool can then be connected to an anchor of an implant, and the insertion tool can be used to push the anchor through the open internal channel. The anchor passes within the open internal channel, and the balance of the implant can be located within the open internal channel alongside the shaft of the insertion tool, or may extend through a longitudinal opening in the tunneler tool to be located externally alongside the tunneler tool. When a desired location of the anchor is achieved, the insertion tool can be used to insert the anchor into supportive tissue. Before or after inserting the anchor into supportive tissue, the tunneler tool can be separated laterally from the insertion tool, and then withdrawn from the tissue path. These steps can be repeated on an opposite side of the patient, using the same or a new set of tools, to place a second anchor of the implant at an opposing supportive tissue location.

According to certain embodiments, a distal end of tool insertion tool 31 fits a distal end opening of tunneler tool 20 to plug the distal end opening during use of the tunneler tool to pass through an incision in a patient and create a tissue path using distal end tip 9. With insertion tool 31 inserted and extended into open internal channel 3 of tunneler tool 20, the assembly of the insertion tool 31 and tunneler tool 20 can be inserted through an incision of the patient and into the interior pelvic region to form a tissue path extending to a location for placement of an end of an implant. As shown at FIG. 7, embodiments of insertion tool 31 can include a proximal end handle 30, a shaft 22, and a distal end tip 23 that fits or plugs a distal end opening of tunneler tool 20. Distal end tip 23 can additionally be useful to engage an implant, such as at an anchor 18, to allow insertion tool 31 to pass the implant or a portion thereof through tunneler tool 20. Shaft 22 is sized and shaped for insertion into tunneler tool 20. Upon insertion of the assembly into the pelvis of the patient through the incision, insertion tool 31 can be removed to leave tunneler tool 20 positioned within the patient to provide a pathway for inserting the implant 12 using the same insertion tool 31.

Optionally, a system 14 can additionally include a core tool (or "plug") 36, or other like device, along with tunneler 20 and insertion tool 31. A core tool can be used to plug a distal end opening of tunneler tool 20 (instead of the insertion tool 31) to prevent tunneler tool 20 from dissecting or "plugging" tissue of the patient during insertion and positioning of tunneler tool 20. As shown at FIG. 7, a core tool 36 can include a proximal end handle 35, a shaft 37, and a distal end tip 39 that fits or plugs a distal end opening of tunneler tool 20. Shaft 37 is sized and shaped for insertion into tunneler tool 20. In use, with core tool 36 inserted and extended into open internal channel 3 of tunneler tool 20, the assembly of the core tool 36 and tunneler tool 20 can be inserted through an incision of the patient and into the interior pelvic region to form a tissue path to a location for placement of an end of an implant. Upon insertion of the assembly into the pelvis of the patient through the incision, core tool 36 can be removed to leave tunneler tool 20 positioned within the patient to provide a pathway for inserting implant 12 using insertion tool 31.

Tunneler tool 20, core tool 36, and insertion tool 31 can be straight, curved, or take on a myriad of other advantageous shapes and configurations. In various embodiments, core tool 36 and insertion tool 31 can be the same tool and operate to position tunneler tool 30, as well as insert the implant 12.

As described in detail elsewhere herein, and as shown at FIG. 7, tunneler tool 20 can include an external communication channel or slot (i.e., longitudinal opening) 5 in communication with open internal channel 3 and also in communication with a distal end opening of tunneler tool 20. In certain embodiments, an anchor 18 of a sling 12 can be adapted to be positioned within internal channel 3, with a portion of the anchor 18 or sling 12 (e.g., mesh 16) extending through longitudinal opening 5, to place a portion of the implant outside of tunneler tool 20 during use.

Figure 8A:
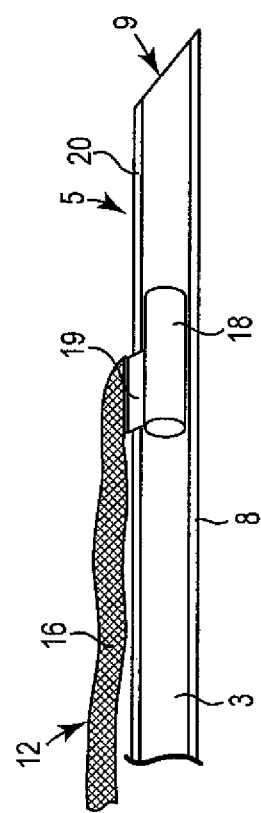
FIGS. 8A and 8B illustrate an exemplary tunneler tool (including a cross sectional view and an end view), having an anchor disposed therein.
Figure 8B:
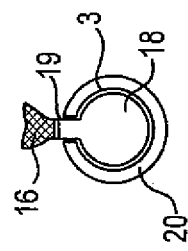

Referring now to FIGS. 8A and 8B, illustrated is an example of a tunneler tool and implant that can be arranged with an anchor of the implant being passed through an open internal channel of the tunneler tool, while another portion of the implant such as an extension portion, extends through a longitudinal opening of the tunneler tool. As shown, anchor 18 is located within open internal channel 3 of tunneler tool 20, and can slide distally or proximally within open internal channel 3, such as by being pushed by a distal end of an insertion tool (not shown) also located within open inner channel 3. Anchor 18 is connected to implant 12 by fin 19, which extends through longitudinal opening 5. This embodiment of tunneler tool 20, implant 12, and anchor 18, allows a major portion of implant 12 to be located outside of tunneler tool 20 during placement of the implant, as insertion tool 31 is within tunneler tool 20 in engagement with anchor 18. Other embodiments allow a major portion of implant 12, or the entire implant, to be located within open internal channel 3 of tunneler tool 20 during placement of the implant, alongside a distal end of an insertion tool 31 engaged with anchor 18 (see, e.g., FIGS. 4A through 4H, and FIG. 5A).

As shown, e.g., at FIGS. 9 through 13, a tunneler tool 20 that includes an elongate opening (slot) 5 can be adapted such that an anchor 18 can be positioned within open internal channel 3 for traversal along the length of tunneler tool 20, while an implant or portion thereof remains outside of open internal channel 3. In various embodiments, the anchor 18 can serve as a plug within the tunneler tool 20, including to plug a distal end opening during insertion of tunneler tool 20, until exiting a distal end. (In other embodiments, a separate plug in the form of a core tool 36 can be used to fill the distal end opening of tunneler tool 20 during insertion of tunneler tool 20 into a patient.) With anchor 18 disposable within the open internal channel 3 of tunneler tool 20, a mesh portion 16 of an implant 12 can be connected to anchor 18 (e.g., via a fin 19) and extend out of tunneler tool 20 through longitudinal opening 5. The insertion tool 31 can be coupled with or otherwise engaged with anchor 18 or another portion of implant 12 such that pushing or advancing insertion tool 31 likewise advances anchor 18 along open internal channel 3 of the tunneler 20. Any desired connector, such as a fin, post, block, plate, etc., or other useful structure, can be used to connect anchor 18, with sling 12 (e.g. mesh 16), with the connector extending through and slidable along longitudinal opening 5. The anchors 18 and sling can be separately attached or integrally molded or joined together.

FIGS. 9 through 13 show various embodiments of anchors 18. Certain embodiments include extendable barbs 40, which can be fixed or adapted to retract or expand as detailed herein. Any of the anchors 18 can include various members, tabs, connectors, lateral extensions, a base, or like features to facilitate the placement, optional expansion, and holding strength of the anchor within tissue, as well as guidance and traversal along or within the open internal channel 3 a tunneler tool 20 during surgical placement of the anchor. Further, the anchors 18 can include various aperture or other mating features at a proximal end to facilitate engagement, or selective engagement, with a distal end 23 of an insertion tool 31.

Figure 9:
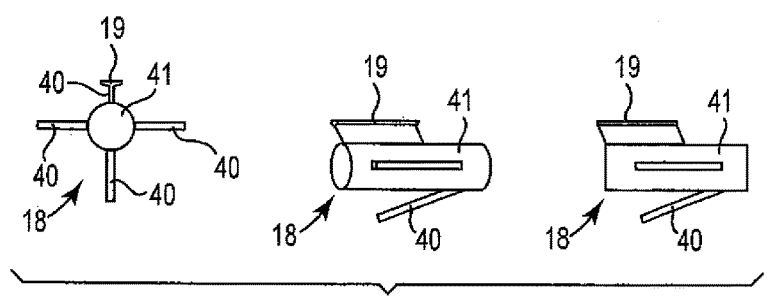
FIGS. 9, 10, 11, 12, and 13 show examples of anchors as described.
Figure 10:
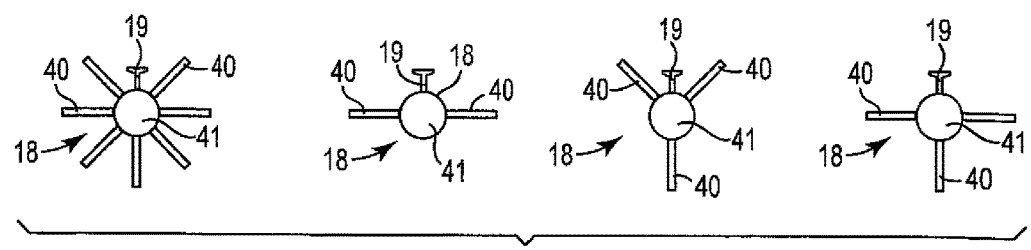

Referring to FIGS. 9 and 10, illustrated are various embodiments (side views and end views) of useful anchors (18). Each of illustrated anchors 18 can include one or more tines or barbs 40 adapted to retract or lay back against an anchor base 41, while anchor 18 is located within open internal channel 3 of tunneler tool 20. The illustrated anchors 18 also include a fin 19 that can extend through a longitudinal opening 5 of a tunneler tool 20, to connect to an implant located outside of the tunneler tool 20. Upon exiting the distal end opening of tunneler tool 20, the bias of retracted barbs 40, while located within open internal channel 3, will cause the barbs 40 to extend outward and increase the cross-sectional size of the anchor 18. Barbs 40 are adapted for tissue penetration while in the non-extended positions, and tissue fixation upon expansion to the extended or expanded positions. Each exemplary anchor 18, at base 41, can include recesses configured to receive retracted barbs 40. Barbs 40 can be constructed of memory shaped plastic or metal materials, include mechanical or living hinges, or can be constructed in other ways to facilitate the operable retraction and expansion features described herein.

Figure 11:
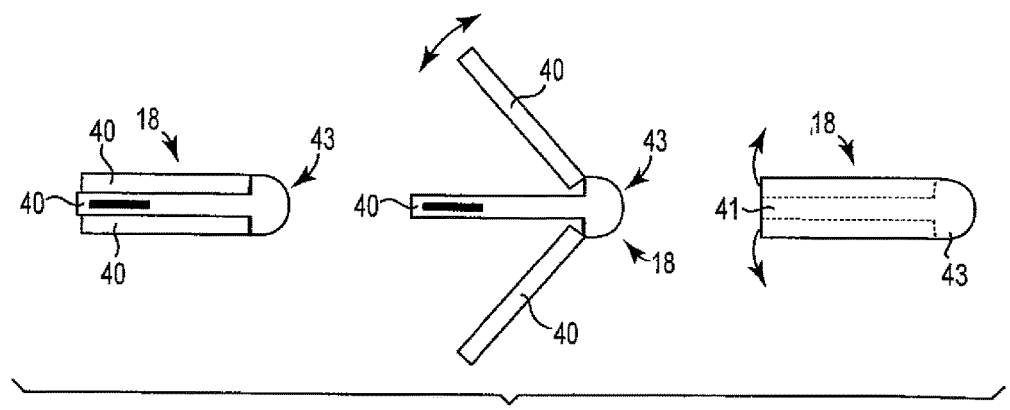

FIG. 11 shows an embodiment of an anchor that includes a distal end 43, and one or more tines or barbs (or extendable lateral extensions) 40 connected to the distal end and adapted to retract or lay back in a retracted position while anchor 18 is located within open internal channel 3 of tunneler tool 20. Anchor 18 does not include a fin (e.g., 19) or other connecting device capable of extending through a longitudinal opening 5 of a tunneler tool 20 to connect to an implant located outside of the tunneler tool 20. Anchor 18 as illustrated also does not include a base (41). Instead of a base 41, tines or barbs 40 can be supported by distal end 43. And, when barbs 40 are in their retracted positions, within an open internal channel 3, the retracted barbs 40 can perform the function of a base and can be used to engage a distal end of an insertion tool to push anchor 18.

Figure 12:
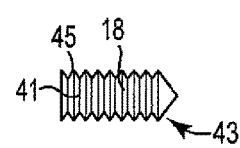

FIG. 12 shows an embodiment of an anchor that includes a distal end 43, a base 41, and a frictional outer surface that includes multiple small ridges or extensions, e.g., teeth 45. Anchor 18, as illustrated, does not include a fin (e.g., 19), but a fin or other connecting device capable of extending through a longitudinal opening of a tunneler tool 20 to connect to an implant located outside of the tunneler tool 20, could be included. Anchor 18 as illustrated also does not include elongate, extendable barb features 40 or other elongate lateral extensions, but instead includes circumferential ridges, teeth, or other frictional structure 45 to allow anchor 18 to be inserted into tissue and subsequently hinder, resist, or prevent removal from the tissue.

Figure 13:
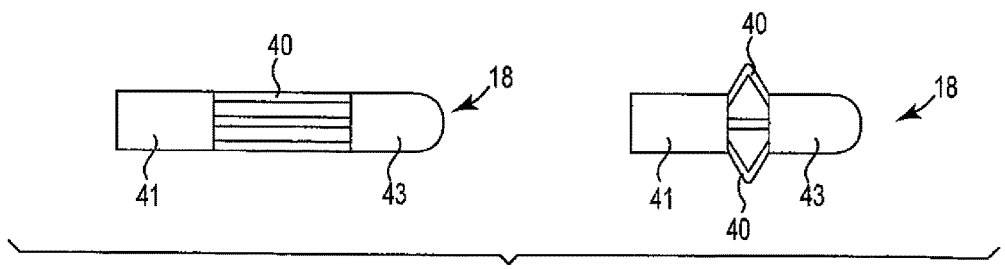

FIG. 13 shows an embodiment of an anchor 18 that includes a distal end 43, base 41, and one or more tines or barbs 40 connected to base 41 and distal end 43. Anchor 18 does not include a fin (e.g., 19) or other connecting device capable of extending through a longitudinal opening of a tunneler tool 20 to connect to an implant located outside of the tunneler tool 20, but a fin or other such structure could be included. Barbs 40 are adapted to retract in a retracted position while anchor 18 is located within open internal channel 3 of tunneler tool 20. Upon exiting the distal end opening of tunneler tool 20, the bias of the retracted barbs 40, while located within open internal channel 3, will cause the barbs 40 to extend outward and increase the cross-sectional size of anchor 18. Barbs 40 are adapted for tissue penetration while in the non-extended positions, and tissue fixation upon expansion to the extended or expanded positions. Barbs 40 can be constructed of metal or polymeric memory shaped materials, include mechanical or living hinges, or can be constructed in other ways to facilitate the operable retraction and expansion features described herein.

Figure 14A:
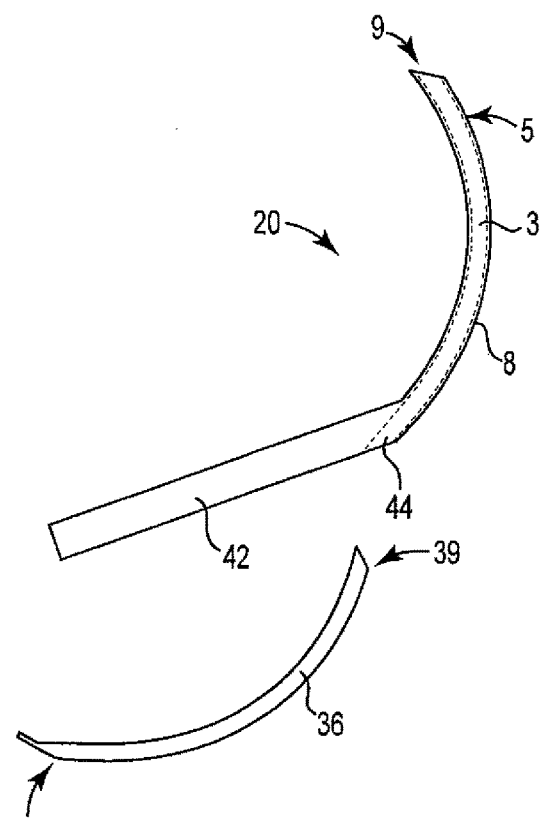
Figure 14B:
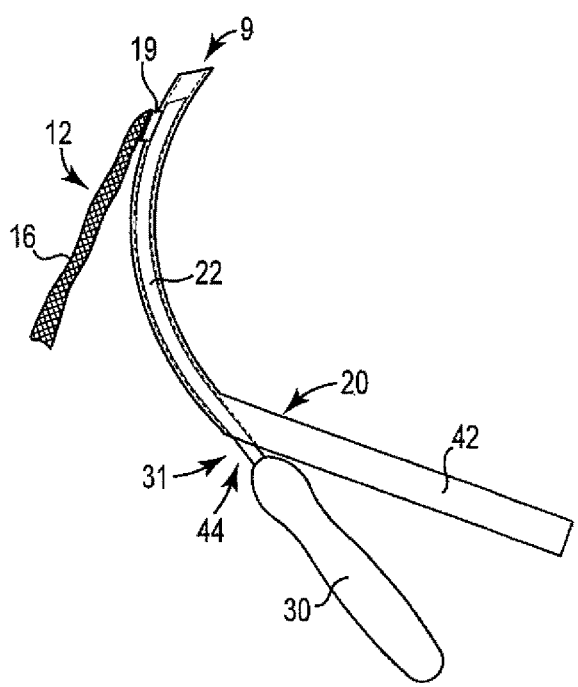

FIGS. 14A and 14B illustrate a delivery tool system, including an implant, that includes a tunneler tool 20, a core tool 36, and an insertion tool 31. As shown in FIG. 14A, tunneler tool 20 can include a handle portion 42, curved shaft 8 (of constant or varied radius) that includes distal end tip 9, open internal channel 3, and longitudinal opening 5. Longitudinal opening 5 is located on the outer curved surface of shaft 8. A communication port or opening (proximal end opening) 44 can be included at a proximal end portion of shaft 8, at a location adjacent to handle 42 meeting a proximal end of shaft 8. This location of proximal end opening 42 facilitates introduction of the insertion tool 31 during a surgical procedure. For example, after placement of shaft 8 through an incision in a patient, proximal end opening 44 can remain external to the patient and accessible to a surgeon or other user.

FIG. 14B illustrates tunneler tool 20 and insertion tool 31 in use, wherein shaft 22 of insertion tool 20, engaged with anchor 18 of implant 12, is introduced through proximal end opening 44 and advanced along open internal channel 3 of tunneler tool 20. Mesh portion 16 is connected to anchor 18 by fin 19 or another connecting structure, and rides outside of and along the outer surface length of tunneler tool 20. Portions or all of tunneler tool 20 and insertion tool 31 can be constructed of a generally flexible material, or a rigid material, to facilitate traversal and component introduction.

FIG. 15 shows an embodiment of insertion tool 31, having shaft 22 that includes one or more angle or bend 48. Also shown is implant 12 having a central mesh portion 16 with integral support portion and extension portions, and two self-fixating tips 18 at opposing ends of the two extension portions. Shaft 22 can be a relatively stiff metal (stainless steel or nitinol) or stiff plastic, attached at proximal end 21 to handle 30, and having distal end 23 adapted to engage a proximal end (e.g., base) of self-fixating tip 18. Shaft 22 includes two bends, 48a and 48b. Each bend is approximately a 90 degree angle, but other angles may also be useful. The combined angles of the bends allow the longitudinal axis of shaft 22 at distal end tip 23 to be parallel with a longitudinal axis of handle 30 (i.e., the sum of the angles of the two bends may be approximately 180 degrees, e.g., from 160 degrees to 200 degrees.

Figure 16A:
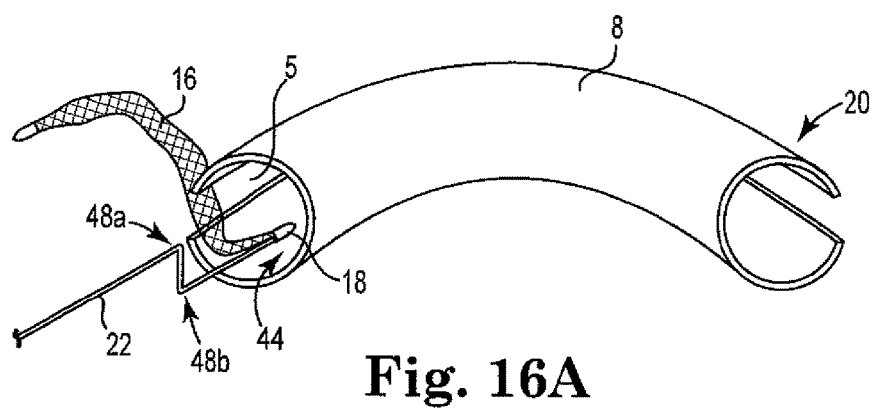
FIGS. 16A, 16B, and 16C show a system that includes the insertion tool of FIG. 15 and a tunneler tool, in use.
Figure 16B:
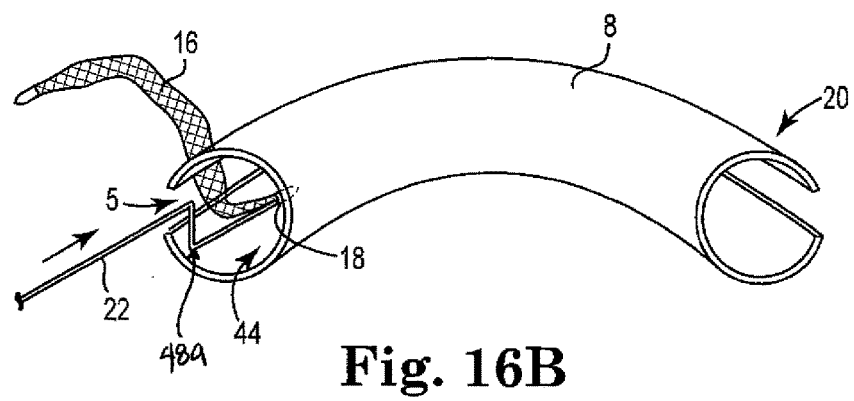
Figure 16C:
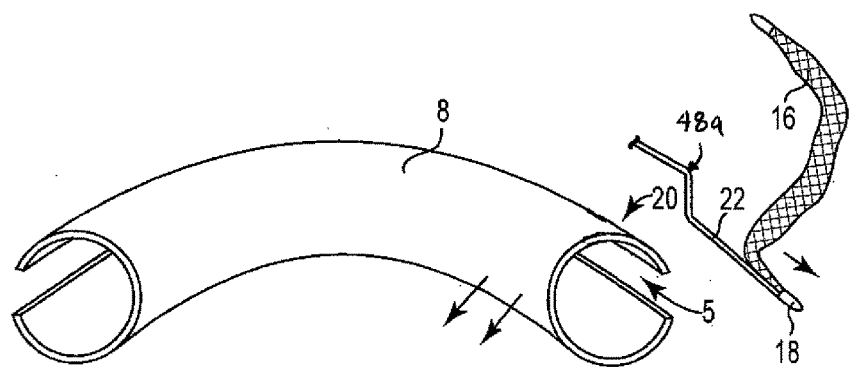

In use, as illustrated at FIGS. 16A, 16B, and 16C, shaft 22, having bends 48a and 48b, allows a distal portion of shaft 22 (distal to both bends, i.e., between distal end 23 and bend 48b) to be positioned within open internal channel 3 of an tunneler tool 20, while a proximal portion of shaft 22 (proximal to both bends, i.e., between handle 30 and bend 48a) is located externally of open inner channel 3. In this manner, bends 48a and 48b may facilitate guidance and use of insertion tool 31 with implant 12 and tunneler tool 20. For instance, bends 48a and 48b can permit maneuvering of a distal portion of shaft 22 through a distal portion of elongate opening (slot) 5 of tunneler tool 20. FIG. 16A shows a distal portion of insertion tool shaft 22, including distal end 23 engaged with anchor 18, entering proximal end opening 44 of tunneler tool 20. The portion of shaft 22 between distal end 23 and bend 48b enters open internal channel 3, and the remaining length of shaft 22 remains exterior to open internal channel 3. Implant 12 and the portion of shaft 22 that extends between bend 48a and bend 48b, pass through longitudinal opening 5 to be located exterior to open internal channel 3. FIG. 16B shows that the assembly of insertion tool 31 and implant 12 can be advanced longitudinally and distally along a length of open internal channel 3, to a distal end of shaft 8 of tunneler tool 20. With implant 12 and anchor 18 located at a desired location at the distal end of tunneler tool 20, and either before or after placement of anchor 18 within supportive tissue, tunneler tool 20 can be withdrawn from the patient by movement of tunneler tool 20 laterally or proximally relative to insertion tool 31 (see arrows), to cause distal end 23 and anchor 18 to separate from the tunneler tool 20, e.g., to pass through longitudinal opening 5.

Accordingly, as illustrated and described herein, the tools, systems, and implants can be useful for treating a pelvic condition by steps that include the following. A tunneler tool can be used to make a tissue path from an incision of a patient to a location of a pelvic region at which an end of an implant is to be secured to supportive tissue. The incision may be an external incision or a vaginal incision, and may be a medial incision (e.g., vaginal or perineal), or otherwise. A distal end of the tunneler tool can be advanced through the incision and advanced through internal tissue of the patient to supportive tissue. Optionally and preferably, a distal end opening of the tunneler tool can be filled (e.g., plugged) to prevent undue trauma to the patient during formation of the tissue path, by the distal end tip and distal end opening of the tunneler tool. The distal end opening may be plugged by placement of a distal end of a core tool at the location of the distal end opening. Alternately, the distal end opening may be plugged by placement of a distal end of an insertion tool at the location of the distal end opening. As yet another alternative, the distal end opening may be plugged by placement of an anchor (e.g., 18, such as a self-fixating tip) at the location of the distal end opening, the anchor being engaged with a distal end of an insertion tool placed within the tunneler tool.

Upon desired placement of the tunneler tool within a patient, a core tool, if used to fill the distal end opening of the tunneler tool, can be removed from the tunneler tool. If an insertion tool (without an anchor engaged at the distal end) was used to fill the distal end opening of the tunneler tool, the insertion tool can be removed from the tunneler tool. (If an insertion tool (with an anchor engaged at the distal end) was used to fill the distal end opening of the tunneler tool, a next step can be to remove the tunneler tool from the patient. See below.)

After placement of the tunneler tool and removal of a core tool or insertion tool used to fill the distal end opening during use of the tunneler tool to produce a tissue path, an implant (or a portion thereof) may be introduced at a proximal end opening of the tunneler tool using an insertion tool. The insertion tool can advance the implant (or a portion thereof) along the length of the tunneler tool shaft, to the distal end of the tunneler tool shaft. The implant may be contained entirely within the tunneler tool, or a portion of the implant may extend through a longitudinal opening to a location external to the tunneler tool. Likewise, a shaft of the insertion tool may be contained entirely within the tunneler tool, or a portion of the shaft may extend through a longitudinal opening to a location external to the tunneler tool and remain external to the tunneler tool.

After placement of the implant (or a portion thereof) at the distal end of the tunneler tool shaft, and at a location for securing to supportive tissue, the tunneler tool can be removed. For example, the tunneler tool may be laterally withdrawn away from any portion of the implant and tunneler tool positioned with the tunneler tool, by aligning the insertion tool with a longitudinal channel of the tunneler tool and laterally separating the tunneler tool from the insertion tool. The insertion tool and implant pass from the open internal channel of the tunneler tool, through the longitudinal opening, and become free of the tunneler tool. The tunneler tool can then be withdrawn in. a proximal direction and removed from the patient.

The insertion tool can be used to place the anchor at supportive tissue, e.g., at tissue of an obturator foramen. This part of the method can be performed either before or after removal of the tunneler tool from the tissue path and the patient, but can preferably be performed according to the latter option, after removal of the tunneler tool from the patient. Advantageously, the latter option allows for the step of placing an anchor at supportive tissue to be separate from a step of creating a tissue path extending to the supportive tissue, from an incision, such as an external incision (e.g., a medial incision).

In use, a system (e.g., 14) described herein can be used bilaterally, to place two ends of an implant in a patient, one end at a right side of the patient and the other end at a left side of the patient, preferably through a single medial incision. A method and techniques described immediately above can be performed on one side of a patient to place a first end of an implant, then on another (opposite) side of a patient to place a second end of an implant. One end or anchor 18 of an implant 12 will be attached at each side of the interior pelvic region of the patient such that a support portion (e.g. mesh 16) extends under tissue or an organ in need of physical support (e.g., urethra, bladder, bladder neck, vaginal tissue, etc.).

According to certain specific embodiments of delivery tool systems, an insertion tool 31 can include two separate but joinable devices 31*a*, 31*b*, i.e., a system can include two separate insertion tools. Each separate insertion tool 31*a* and 31*b* can include a handle 30, shaft 22, distal end 23, or other features and components described herein as a feature of an insertion tool 31. However, as shown in FIGS. 19 through 22, a portion of each of insertion tool 31*a*, 31*b* can be adapted to link or otherwise connect to the other insertion tool. Joining surfaces 51*a* and 51*b* can be located at a proximal end of an insertion tool 31, such as at opposing and joinable surfaces of opposing handles, and can include complementary joining surfaces that when engaged will limit, inhibit, or prevent relative movement between the surfaces in at least one direction.

Figure 17D:
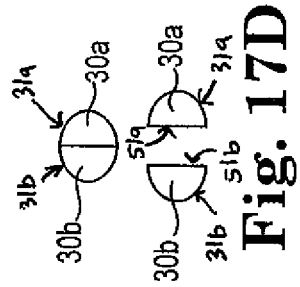
FIGS. 17A (top view), 17B (top view), 17C (top view), 17D (end view), and 17E (side views), illustrate insertion tools as described.
Figure 17E:
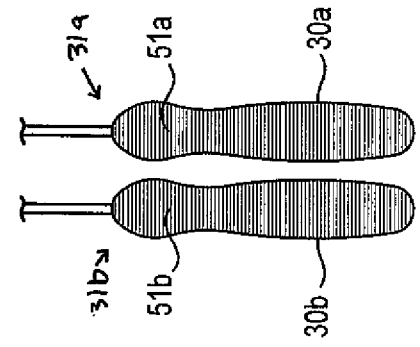
Figure 17C:
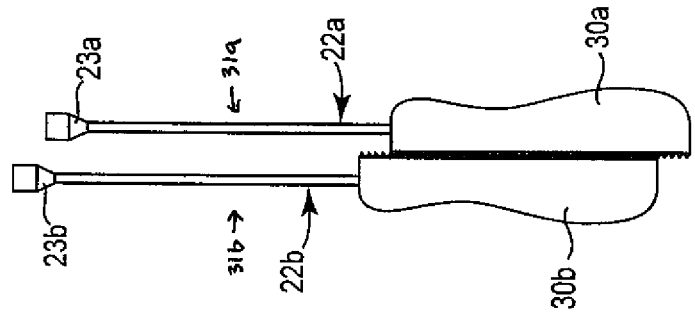
Figure 17B:
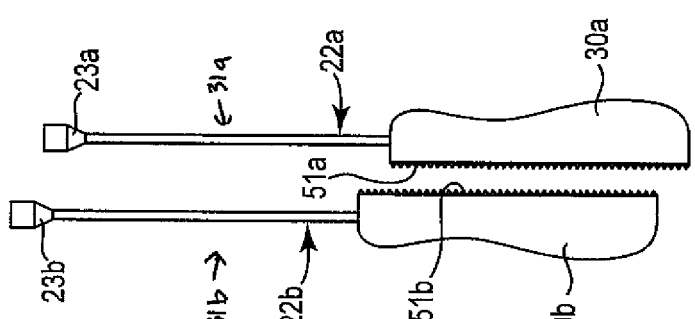
Figure 17A:
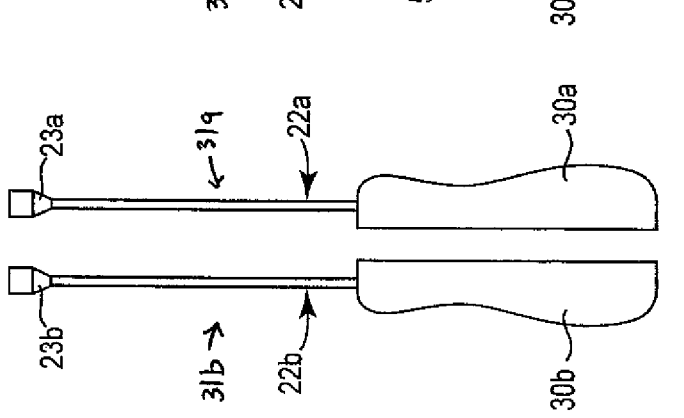

Joining surfaces 51*a* and 51*b* may include complementary and opposing engagement surfaces having opposing gears, teeth, interacting surfaces, pins, members, slots, frictional features, and other like features to facilitate a frictional engagement, linkage, joining, selective connectivity, and optional locking of the two insertion tools 31*a* and 32*b*. See FIGS. 17A, 17B, 17C, 17D, and 17E, and FIGS. 18A, 18B, 18C, 18D, 18E, and 18F. FIGS. 17B and 17C show top views of insertion tools 31*a* and 31*b* having joinable surfaces 51*a* and 51*b*, wherein the joinable surfaces comprise a series of teeth or ridges, with the joinable surfaces disengaged (FIG. 17B) or engaged (FIG. 17C). FIG. 17E shows side views (each insertion tool is rotated ninety degrees) of insertion tools 31 a and 31 b having joinable surfaces 51*a* and 51*b*. FIGS. 18A and 18B show top and side views, respectively, of insertion tools 31*a* and 31*b* having joinable surfaces 51*a* and 51*b*, wherein the joinable surfaces comprise an elongate peg and an opposing elongate channel, allowing for some relative longitudinal movement when surfaces 51*a* and 51*b* are joined. FIGS. 18C and 18D show top and side views, respectively, of insertion tools 31*a* and 31*b* having joinable surfaces 51*a* and 51*b* comprising a series of peg extensions and opposing complementary holes. FIGS. 18E and 18F show top and side views, respectively, of insertion tools 31*a* and 31*b* having joinable surfaces 51*a* and 51*b* comprising a series of gear extensions and opposing complementary channels.

Figure 19:
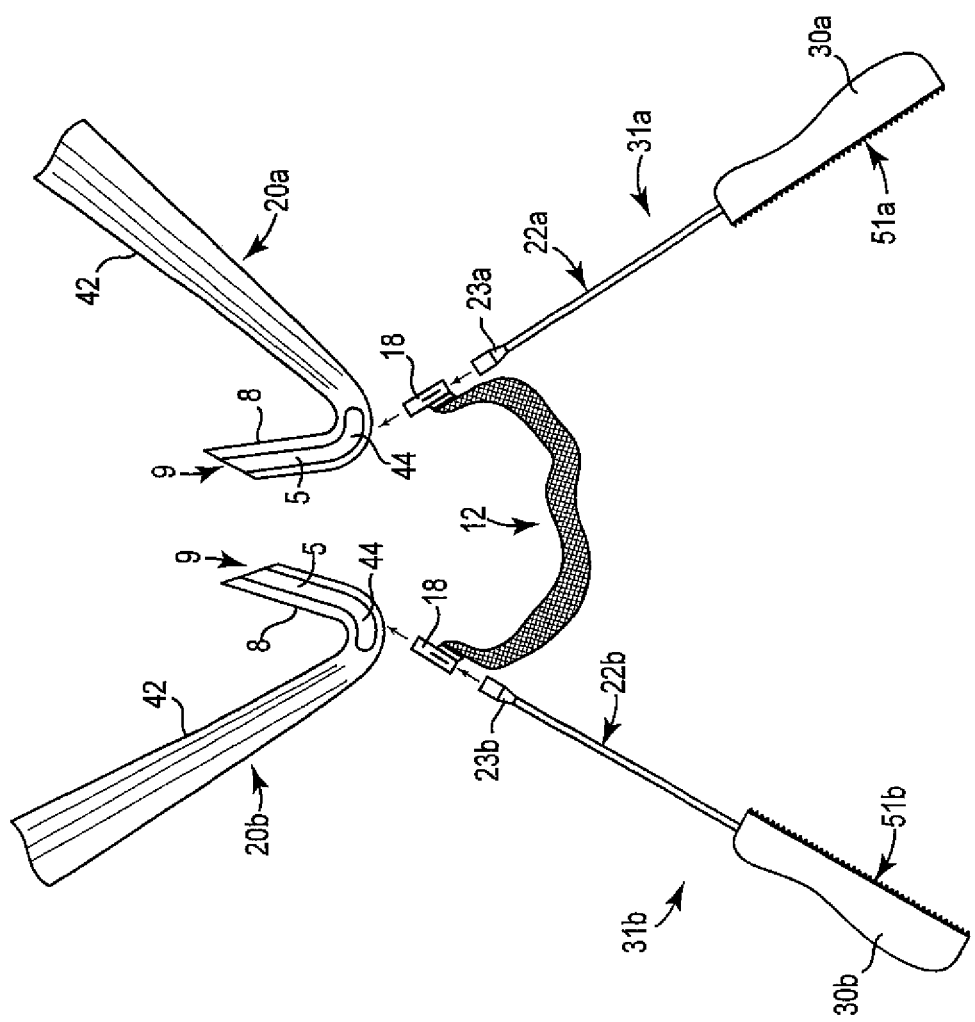
FIGS. 19 and 20 illustrate a system as described, including two tunneler tools and two insertion tools, along with an implant.

In use, each of the two individual insertion tools 31*a* and 31*b* can be used separately, without joining their respective joining surfaces 51*a* and 51*b*, with each tool being used, via a single incision, to place an end of an implant at two desired supportive tissue locations on two opposing sides a patient. See, e.g., FIGS. 19 and 20. For example, one insertion tool can be useful to place an end of an implant, through an incision, at or near supportive tissue on a left side of a patient, e.g., at a left obturator foramen. Using the same medial or external incision, the other insertion tool can be useful to place a second end of the implant at or near opposing supportive tissue on a right side of the patient, e.g., at a right obturator foramen. FIG. 19 shows two tunneler tools, 20*a* and 20*b*, one for a right side of a patient and one for a left side of the patient. FIG. 19 also shows two insertion tools, 31*a* and 31*b*. Each set of tools can be the same, and can include a shaft that is either straight or curved, or one tunneler tool and one insertion tool can be specifically designed for use on a right side of a patient and the other tunneler tool and the other insertion tool can be specifically designed for use on the left side of the patient.

Figure 20:
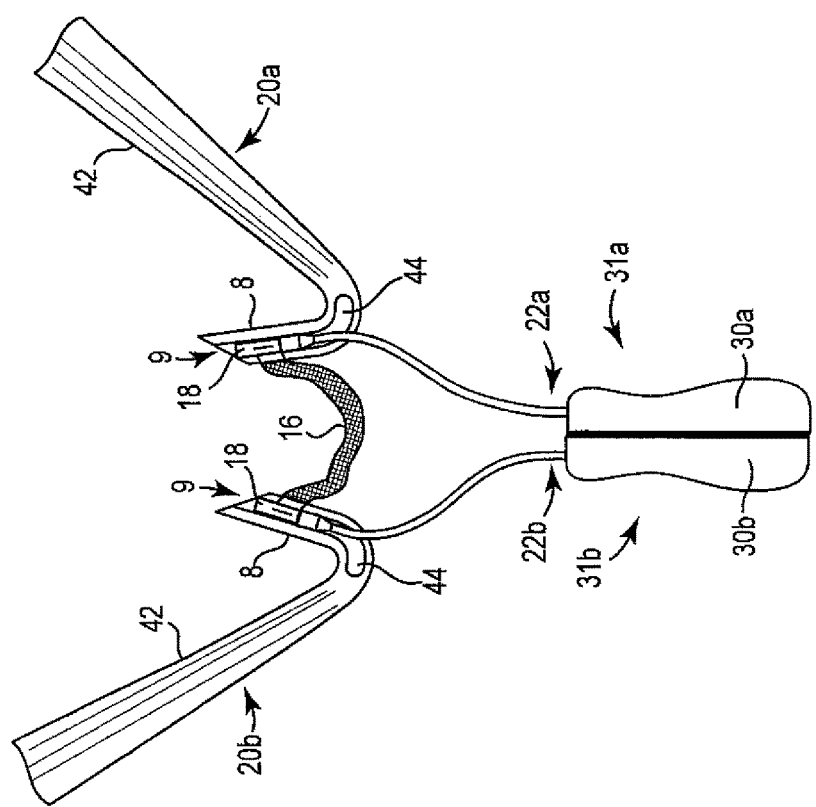

Insertion tools 31*a* and 3*ab* can be used independently of each other, as stated, during insertion, until the user desires to manipulate ends or anchors 18 of implant 12 together. FIG. 19 shows insertion tools 31*a* and 31*b* in a predeployment configuration with handles 30*a* and 30*b* separated. FIG. 20 shows the same insertion tools 31*a* and 31*b* after formation of a tissue path, during placement of implant 12 (i.e., anchors 18) through tunneler tools 20, such that barbs 40 of anchors 18 can expand upon exiting the distal end openings of the respective tunneler tools 20. During deployment, before or after removal of the two tunneler tools 20, handles 30*a* and 30*b* can be contacted and joined, to likewise join insertion tools 31a and 31b. With insertion tools 31a and 31b joined at handles 20a and 30b, and optionally with removal of the two tunneler tools 20, the user can grasp both insertion tools (31a and 31b), to allow the user to manipulate and control both handles with a single hand. The user can have combined control of both the left side anchor 18 and the right side anchor 18 of implant 12, to improve control of the placement and tensioning of the implant being surgically installed.

Various shapes and configurations for the tunnelers 20, insertion tools 31 and other components and tools are envisioned depending on the particular surgical application or anatomy of the patient (male or female).

A variety of materials may be used to form portions or components of the system 14, including nitinol, polymers, elastomers, thermoplastic elastomers, metals, ceramics, springs, wires, plastic tubing, and the like. The system 14 and its components and methods may have a number of suitable configurations known to one of ordinary skill in the art.

All patents, patent applications, and publications cited herein are hereby incorporated by reference in their entirety as if individually incorporated, and include those references incorporated within the identified patents, patent applications and publications.

Numerous modifications and variations of the present invention are possible in light of the teachings herein. It is therefore to be understood that within the scope of the appended claims, the invention may be practiced other than as specifically described herein.

The invention claimed is:

1. A delivery tool system comprising:
a tunneler tool comprising:
a tunneler shaft comprising a proximal end, a distal end, and an internal channel,
a distal end having a beveled distal end tip adapted to create a tissue path,
a distal end opening at the distal end of the tunneler shaft and in communication with the internal channel, and
a fixed longitudinal opening along a length of the tunneler shaft and extending to the distal end to connect to the distal end opening; and
an insertion tool comprising a proximal end, a distal end, and an elongate shaft between the proximal end and the distal end, wherein at least the distal end of the insertion tool can be located within the internal channel of the tunneler tool, the elongate shaft of the insertion tool including a recessed region disposed on one side of the elongate shaft, the recessed region configured to receive at least a portion of an implant, the recessed region including a first portion with a first width and a second portion having a second width, the second portion being located distally from the first portion, the second width being smaller than the first width,
wherein a distal portion of the elongate shaft of the insertion tool is capable of being positioned within the internal channel, and is capable of being removed from the internal channel by passing through the longitudinal opening.

2. The delivery tool system according to claim 1, wherein the distal portion of the elongate shaft of the insertion tool is capable of:
being inserted into the internal channel at a proximal end of the tunneler shaft,
being advanced within the internal channel to the distal end of the tunneler shaft, and
being removed from the internal channel by passing laterally through the longitudinal opening.

3. The delivery tool system according to claim 1, wherein the elongate shaft of the insertion tool has a length greater than a length of the tunneler shaft, and comprises a cross-sectional dimension that allows the elongate shaft to pass through the longitudinal opening.

4. The delivery tool system according to claim 1, wherein the internal channel has a non-circular cross section along a length between the proximal end and the distal end of the tunneler shaft.

5. The delivery tool system according to claim 1, wherein the insertion tool comprises at least one indexer located along a length of the elongate shaft, each indexer having a first cross-sectional dimension that is greater than a width of the longitudinal opening, and a second cross-sectional dimension that is less than the width of the longitudinal opening.

6. The delivery tool system according to claim 1, wherein the insertion tool is a first insertion tool having a first handle, the delivery tool system further comprising:
a second insertion tool having a second handle, wherein the first handle and the second handle comprise joinable surfaces, wherein the joinable surfaces are capable of being engaged to inhibit relative longitudinal movement between the first insertion tool and the second insertion tool.

7. The delivery tool system according to claim 1, further comprising:
a core tool, the core tool comprising an elongate shaft, a proximal end, and a distal end adapted to plug the distal end opening of the tunneler tool.

8. The delivery tool system according to claim 1, wherein the distal end of the insertion tool is adapted to plug the distal end opening.

9. The delivery tool system according to claim 1, wherein the implant includes a tissue support portion, an extension portion extending from the tissue support portion and comprising a distal end, and an anchor at the distal end of the extension portion, the anchor adapted to pass within the internal channel, wherein the distal end of the insertion tool is adapted to engage the anchor in a manner to allow the insertion tool to push the anchor through the internal channel.

10. The delivery tool system according to claim 9, wherein the implant is adapted to extend from a first anchor located at a first obturator foramen of a patient, with the support portion extending below a urethra of the patient, to a second anchor located at an opposite obturator foramen of the patient.

11. A method of treating a pelvic condition in a patient, the method comprising:
providing the delivery tool system as recited at claim 1; and
using the delivery tool system to place the implant in the patient to treat the pelvic condition.

12. The delivery tool system according to claim 1, wherein the longitudinal opening extends along a portion of the length at the distal end of the tunneler tool.

13. The delivery tool system according to claim 1, wherein the longitudinal opening extends along an entire length between the proximal end of the tunneler tool and the distal end of the tunneler tool.

14. The delivery tool system according to claim 1, wherein the recessed region is located proximate to the proximal end of the insertion tool.

15. The delivery tool system according to claim 1, wherein the recessed region extends along a majority of a length of the elongated shaft of the insertion tool.

16. A delivery tool system comprising:
a first tunneler tool comprising:
a tunneler shaft comprising a proximal end, a distal end, and an internal channel,
a distal end having a beveled distal end tip adapted to create a tissue path,
a distal end opening at the distal end of the tunneler shaft and in communication with the internal channel,
a fixed longitudinal opening along a length of the tunneler shaft and extending to the distal end to connect to the distal end opening;
a second tunneler tool comprising:
a tunneler shaft comprising a proximal end, a distal end, and an internal channel,
a distal end opening at the distal end of the tunneler shaft and in communication with the internal channel,
a fixed longitudinal opening along a length of the tunneler shaft and extending to the distal end to connect to the distal end opening;
a first insertion tool comprising a proximal end, a distal end, and an elongate shaft between the proximal end and the distal end, wherein at least the distal end of the first insertion tool can be located within the internal channel of the first tunneler tool and can be removed from the internal channel by passing through the fixed longitudinal opening of the first tunneler tool, the elongated shaft of the first insertion tool including a recessed region disposed on one side of the elongated shaft, the recessed region configured to receive at least a portion of an implant, the recessed region including a first portion with a first width and a second portion having a second width, the second portion being located distally from the first portion, the second width being smaller than the first width; and
a second insertion tool comprising a proximal end, a distal end, and an elongate shaft between the proximal end and the distal end, wherein at least the distal end of the second insertion tool can be located within the internal channel of the second tunneler tool and can be removed from the internal channel by passing through the fixed longitudinal opening of the second tunneler tool.

17. The delivery tool system according to claim 16, wherein the first insertion tool comprises a first handle, and the second insertion tool comprising a second handle, wherein the first handle and the second handle comprise joinable surfaces.

18. The delivery tool system according to claim 17, wherein the joinable surfaces are capable of being engaged to inhibit relative longitudinal movement between the first handle and the second handle.

19. The delivery tool system according to claim 16, in combination with the implant, the implant comprising a support portion, two extension portions, and an anchor at an end of each extension portion, at least one of the anchors being adapted to engage the distal end of at least one of the first insertion tool and the second insertion tool.

20. The delivery tool system according to claim 16, wherein the longitudinal opening of the first tunneler tool extends along a portion of the length at the distal end of the first tunneler tool and the longitudinal opening of the second tunneler tool extends along a portion of the length at the distal end of the second tunneler tool.

21. A delivery tool system comprising:
a tunneler tool comprising:
a tunneler shaft comprising an open proximal end, a distal end, and an internal channel,
a distal end having a beveled distal end tip adapted to create a tissue path,
a distal end opening at the distal end of the tunneler shaft and in communication with the internal channel,
a fixed longitudinal opening along a length of the tunneler shaft and extending to the distal end to connect to the distal end opening;
an insertion tool comprising a proximal end, a distal end, and an elongate shaft between the proximal end and the distal end, wherein the insertion tool can be located within the internal channel of the tunneler tool and is capable of being removed from the internal channel by passing through the fixed longitudinal opening of the tunneler tool, the elongated shaft of the insertion tool including a recessed region disposed on one side of the elongated shaft, the insertion tool including at least one indexer located along a length of the elongate shaft, the at least one indexer having a first cross-sectional dimension that is greater than a width of the fixed longitudinal opening, and a second cross-sectional dimension that is less than the width of the fixed longitudinal opening;
a core tool comprising an elongate shaft and a distal end that comprises a plug, the elongate shaft of the core tool being adapted to extend within a length of the internal channel, and the plug being adapted to close the distal end opening; and
an implant comprising a support portion, two extension portions, and an anchor at an end of each extension portion, at least one anchor being adapted to engage the distal end of the insertion tool, at least a portion of the implant configured to be disposed within the recessed region.

* * * * *